United States Patent
Wang et al.

(10) Patent No.: US 10,690,782 B2
(45) Date of Patent: Jun. 23, 2020

(54) SYSTEMS AND METHODS FOR POSITRON EMISSION TOMOGRAPHY IMAGE RECONSTRUCTION

(71) Applicant: UIH AMERICA, INC., Houston, TX (US)

(72) Inventors: Jizhe Wang, Houston, TX (US); Hongdi Li, Houston, TX (US); Tao Feng, Houston, TX (US)

(73) Assignee: UIH AMERICA, INC., Houston, TX (US)

( * ) Notice: Subject to any disclaimer, the term of this patent is extended or adjusted under 35 U.S.C. 154(b) by 315 days.

(21) Appl. No.: 15/721,783

(22) Filed: Sep. 30, 2017

(65) Prior Publication Data
US 2019/0101655 A1 Apr. 4, 2019

(51) Int. Cl.
*G01T 1/166* (2006.01)
*G06K 9/00* (2006.01)
(Continued)

(52) U.S. Cl.
CPC ............ *G01T 1/1663* (2013.01); *A61B 6/037* (2013.01); *A61B 6/5205* (2013.01); *G01R 33/28* (2013.01);
(Continued)

(58) Field of Classification Search
USPC ........ 382/100, 103, 106–107, 128–134, 154, 382/162, 168, 173, 181, 190, 220, 209, 382/224, 232, 254, 27, 4, 285–291, 305, 382/274; 600/427; 250/363.03, 363.04; 378/4, 21
See application file for complete search history.

(56) References Cited

U.S. PATENT DOCUMENTS 6,147,353 A * 11/2000 Gagnon ................ G01T 1/1648
250/363.04
6,490,476 B1 * 12/2002 Townsend ............. A61B 6/032
250/363.03
(Continued)

OTHER PUBLICATIONS

Gerhard W. Goerres et al. PET-CT Image Co-Registration in the Thorax: Influence of Respiration. European Journal of Nuclear Medicine, vol. 29, No. 3, pp. 351-360, Mar. 2002.
(Continued)

*Primary Examiner* — Seyed H Azarian
(74) *Attorney, Agent, or Firm* — Metis IP LLC

(57) ABSTRACT

The disclosure relates to PET imaging systems and methods. The systems may execute the methods to obtain an anatomical image of a subject acquired when the subject remains in a breath-hold status; obtain PET data of the subject, the PET data corresponding to a respiration signal with a plurality of respiratory phases of the subject, the respiratory phases including a first respiratory phase and a second respiratory phase; gate the PET data; reconstruct a plurality of gated PET images, the plurality of gated PET images including a first gated PET image corresponding to the first respiratory phase and a second gated PET image corresponding to the second respiratory phase; determine a first motion vector field between the first gated PET image and the second gated PET image; determine a second motion vector field between the anatomical image and the second gated PET image; and reconstruct an attenuation corrected PET image.

20 Claims, 12 Drawing Sheets

(51) Int. Cl.
  *G01T 7/00* (2006.01)
  *G01R 33/28* (2006.01)
  *G01T 1/29* (2006.01)
  *A61B 6/03* (2006.01)
  *A61B 6/00* (2006.01)
  *G01R 33/48* (2006.01)

(52) U.S. Cl.
  CPC ............ *G01T 1/2992* (2013.01); *G01T 7/005* (2013.01); *G01R 33/481* (2013.01)

(56) References Cited

U.S. PATENT DOCUMENTS

| | | | | |
|---|---|---|---|---|
| 8,569,706 | B2* | 10/2013 | Thiruvenkadam | A61B 6/037 250/363.03 |
| 9,451,926 | B2* | 9/2016 | Kinahan | A61B 6/527 |
| 9,582,906 | B2 | 2/2017 | Ra et al. | |
| 2012/0078089 | A1* | 3/2012 | Wollenweber | A61B 6/032 600/427 |
| 2018/0174333 | A1 | 6/2018 | Feng et al. | |
| 2018/0174360 | A1 | 6/2018 | Feng et al. | |

OTHER PUBLICATIONS

This Month in JNM, The Journal of Nuclear Medicine, vol. 49, No. 8, pp. 11A-12A, Aug. 2008.

Tao Sun et al. Techniques for Respiration-Induced Artifacts Reductions in Thoracic PET/CT. Quantitative Imaging in Medicine and Surgery, vol. 2, No. 1, pp. 46-52, Mar. 2012.

Tsuyoshi Kawano et al., Deep-Inspiration Breath-Hold PET/CT of Lung Cancer: Maximum Standardized Uptake Value Analysis of 108 Patients, J Nucl Med., 49(8):1223-1231, 2008.

\* cited by examiner

600

| Obtaining a CT image corresponding to a scanning area of a subject acquired when the subject remains in a deep inspiration breath-hold status | ～610 |

↓

| Obtaining PET data corresponding to the same scanning area of the subject acquired when the subject being in a breathing status | ～620 |

↓

| Gating the PET data to reconstruct a plurality of gated PET images corresponding to a plurality of respiratory phases, the gated PET images including a first gated PET image corresponding to a first respiratory phase and a second gated PET image corresponding to a second respiratory phase, the first respiratory phase being an end-expiratory phase and the second respiratory phase being an end-inspiratory phase | ～630 |

↓

| Registering the first gated PET image with the second gated PET image | ～640 |

↓

| Determining a first motion vector field between the first gated PET image and the second gated PET image based on the registration | ～650 |

↓

| Determining a second motion vector field between the second gated PET image and the CT image based on the first motion vector field | ～660 |

↓

| Reconstructing an attenuation corrected PET image based on the CT image, the PET data(or the gated PET data), and the second motion vector field | ～670 |

Obtaining a respiration signal of the subject during the PET scan, the respiration signal corresponding to a plurality of respiratory phases of the subject, the respiratory phases including an end-expiration phrase and an end-inspiratory phase ~810

Gating the PET data based on the plurality of respiratory phases of the respiration signal ~820

Reconstructing the gated PET data to obtain a plurality of gated PET images corresponding to the plurality of respiratory phases, the plurality of gated PET images including a first gated PET image corresponding to the end-expiratory phase and a second gated PET image corresponding to the end-expiratory phase ~830

Determining a plurality of candidate CT images based on the CT image and the first motion vector field between the first gated PET image and the second gated PET image ~910

For each of the candidate CT images, determining a similarity between the candidate CT image and the second gated PET image ~920

Identifying a highest similarity among the determined similarities ~930

Determining, based on the identified highest similarity, the second motion vector field between the second gated PET image and the CT image ~940

FIG. 9

SYSTEMS AND METHODS FOR POSITRON EMISSION TOMOGRAPHY IMAGE RECONSTRUCTION

TECHNICAL FIELD

The present disclosure generally relates to systems and methods for image processing, and more specifically relates to methods and systems for reconstructing a Positron emission tomography (PET) image.

BACKGROUND

PET is a specialized radiology procedure that generates three-dimensional images of functional processes in a target organ or tissue of a subject. Specifically, in PET studies, biologically active molecules carrying radioactive tracer molecules are first introduced into the subject. The PET system then detects pairs of gamma rays emitted indirectly by the tracer and reconstructs a three-dimensional image of the tracer concentration within the subject by analyzing the detected signals. Because the biologically active molecules used in PET studies are natural substrates of metabolism at the target organ or tissue, PET can evaluate the physiology (functionality) of the target organ or tissue, as well as its biochemical properties. Changes in these properties of the target organ or tissue may provide information for the identification of the onset or progression of a disease before an anatomical change relating to the disease become detectable by other diagnostic tests, such as computed tomography (CT) or magnetic resonance imaging (MRI).

Furthermore, the high sensitivity of PET—in the picomolar range—may allow the detection of small amounts of radio-labeled markers in vivo. PET may be used in conjunction with other diagnostic tests to achieve simultaneous acquisition of both structural and functional information of the subject. Examples include a PET/CT hybrid system, a PET/MR hybrid system.

PET and CT data of a subject may be obtained using a PET/CT hybrid system. The CT data may be applied in the attenuation correction of the PET data. During a scan in the PET/CT system, a subject may undergo respiratory motion. When the scanning is performed for chest or upper abdomen examinations, respiratory motion of the lungs and/or cardiac motion of the heart of the subject may lead to a mismatch between the PET data and the CT data. The mismatch may subsequently cause artifacts in the PET image, which in turn may affect an interpretation of the PET image, or a diagnosis performed on the basis of the PET image. A CT scan is quick so that the subject may be asked to hold his or her breath during the CT scan. A PET scan is relatively slow and the subject needs to breathe during the PET scan, which may lead to a mismatch between the CT data and the PET data. Thus, it is desirable to develop a method and system for matching the CT data acquired when the subject is in a breath-hold status and the PET data acquired when the subject is in a breathing status to reduce the effect of respiratory and/or cardiac motion of the subject and improve the quality of a PET image reconstructed accordingly.

SUMMARY

According to an aspect of the present disclosure, a method may include obtaining an anatomical image of a scanning area of a subject acquired when the subject remains in a breath-hold status, and obtaining PET data of the scanning area of the subject. The PET data may correspond to a respiration signal with a plurality of respiratory phases of the subject, the respiratory phases including a first respiratory phase and a second respiratory phase. The method may also include gating the PET data into a plurality of bins based on the plurality of respiratory phases of the respiration signal, and reconstructing a plurality of gated PET images corresponding to the plurality of respiratory phases based on the gated PET data. The plurality of gated PET images may include a first gated PET image corresponding to the first respiratory phase and a second gated PET image corresponding to the second respiratory phase. The method may further include determining a first motion vector field between the first gated PET image and the second gated PET image, and determining a second motion vector field between the anatomical image and the second gated PET image based on the first motion vector field. The method may further include reconstructing an attenuation corrected PET image based on the PET data, the second motion vector field, and the anatomical image.

In some embodiments, the breath-hold status may be a deep inspiration breath-hold status, the first respiratory phase may be an end-expiratory phase, and the second respiratory phase may be an end-inspiratory phase. Alternatively, the breath-hold status may be a deep expiration breath-hold status, the first respiratory phase may be the end-inspiratory phase, and the second respiratory phase may be the end-expiratory phase.

In some embodiments, the determining a first motion vector field between the first gated PET image and the second gated PET image may include registering the first gated PET image with the second gated PET image; and determining the first motion vector field based on the registration between the first gated PET image and the second gated PET image.

In some embodiments, the attenuation corrected PET image may correspond to a reference respiratory phase. The reconstructing the attenuation corrected PET image may include determining the reference respiratory phase among the plurality of respiratory phases, and obtaining a reference gated PET image corresponding to the reference respiratory phase among the plurality of gated PET images. The reconstructing the attenuation corrected PET image may also include determining a third motion vector field between each gated PET image and the reference gated PET image, and reconstructing a first PET image corresponding to each respiratory phase based on the second motion vector field. The reconstructing the attenuation corrected PET image may further include transforming the first PET image corresponding to each respiratory phase to a second PET image corresponding to the reference respiratory phase based on the corresponding third motion vector field, and generating the attenuation corrected PET image corresponding to the reference respiratory phase based on the plurality of second PET images.

In some embodiments, the method may further include transform the attenuation corrected PET image corresponding to the reference phase to an attenuation corrected PET image corresponding to one of the plurality of respiratory phases based on the corresponding third motion vector between the respiratory phase and the reference respiratory phase.

In some embodiments, the reconstructing a first PET image corresponding to each of the plurality of respiratory phases may include the following operations for each gated PET image: determining a fourth motion vector field between the gated PET image and the second gated PET image; determining a fifth motion vector field between the gated PET image and the anatomical image based on the fourth motion vector field and the second motion vector field; correcting the anatomical image based on the fifth motion vector field to obtain a corrected anatomical image corresponding to the respiratory phase; and reconstructing a first PET image corresponding to the respiratory phase based on the gated PET data and the corrected anatomical image.

In some embodiments, the attenuation corrected PET image may correspond to an average of the plurality of respiratory phases. The reconstructing the attenuation corrected PET image may include reconstructing, for each respiratory phase, a first PET image corresponding to the respiratory phase; and obtaining the attenuation corrected PET image corresponding to the average of the plurality of respiratory phases by summing the first images corresponding to the plurality of respiratory phases.

In some embodiments, the attenuation corrected PET image may correspond to an average of the plurality of respiratory phases. The reconstructing the attenuation corrected PET image may include generating a corrected anatomical image corresponding to each respiratory phase, and generating an average corrected anatomical image by summing the corrected anatomical images corresponding to the plurality of respiratory phases. The reconstructing the attenuation corrected PET image may also include reconstructing the attenuation corrected PET image corresponding to the average of the plurality of respiratory phases based on the PET data and the average corrected anatomical image.

In some embodiments, the determining a second motion vector field between the second gated PET image and the anatomical image may include: determining a plurality of candidate anatomical images based on the anatomical image and the first motion vector field; determining a similarity between the second gated PET image and each candidate anatomical image; identifying a highest similarity among the determined similarities; and determining the second motion vector field between the second gated PET image and the candidate anatomical image associated with the highest similarity based on the identified highest similarity.

In some embodiments, the determining the similarity between the second gated PET image and each of the candidate anatomical images may be based on at least of a pixel-based similarity, an entropy-based similarity, a mutual information similarity, or a contour-based similarity.

In some embodiments, the anatomical image may be at least one of a computed tomography (CT) image or a magnetic resonance (MR) image.

In some embodiments, the plurality of respiratory phases may be determined based on an amplitude or a time interval of a motion represented in the respiration signal.

In some embodiments, the registering the first gated PET image with the second gated PET image may be based on at least one of an optical flow registration algorithm, a demons registration algorithm, or a B-spline registration algorithm.

According to another aspect of the present disclosure, a system may include at least one processor and storage for storing instructions. When executed by the at least one processor, the instructions may cause the system to perform a method. The method may include obtaining an anatomical image of a scanning area of a subject, the anatomical image being unaffected by respiratory motion; and obtaining PET data of the scanning area of the subject, the PET data being affected by a respiratory motion of the subject. The method may also include binning the PET data into a plurality of respiratory phases of the respiratory motion of the subject; and reconstructing a plurality of gated PET images based on the binned PET data. The method may further include determining a target motion vector field between the anatomical image and a target gated PET image among the plurality of gated PET images; and generating an attenuation corrected target gated PET image by performing a phase-matched attenuation correction on the target gated PET image based on the anatomical image and the target motion vector field.

In some embodiments, the plurality of respiratory phases may include a first respiratory phase and a second respiratory phase. The anatomical image may be acquired when the subject remains in a deep inspiration breath-hold status, the first respiratory phase may be an end-expiratory phase, and the second respiratory phase may be an end-inspiratory phase. Alternatively, the anatomical image may be acquired when the subject remains in a deep expiration breath-hold status, the first respiratory phase may be the end-inspiratory phase, and the second respiratory phase may be the end-expiratory phase.

In some embodiments, the determining a target motion vector field between the anatomical image and a target gated PET image of among the plurality of gated PET images may include: determining a first motion vector field between a first gated PET image corresponding to the first respiratory phase and a second gated PET image corresponding to the second respiratory phase; determining a second motion vector field between the anatomical image and the second gated PET image based on the first motion vector field; and determining the target motion vector field between the anatomical image and the target gated PET image based on the first motion vector field and the second motion vector field.

In some embodiments, the generating an attenuation corrected target gated PET image by performing a phase-matched attenuation correction on the target gated PET image may include: determining a phase-matched anatomical image corresponding to the target gated PET image by applying the target motion vector field to the anatomical image; performing the phase-matched attenuation correction on the target gated PET image based on the phase-matched anatomical image to generate the attenuation corrected target gated PET image.

In some embodiments, the phase-matched anatomical image and the target gated PET data may correspond to a same respiratory phase.

According to another aspect of the present disclosure, a system may include at least one storage medium including a set of instructions, and at least one processor configured to communicate with the at least one storage medium. When executing the set of instructions, the system may be directed to obtain an anatomical image of a scanning area of a subject acquired when the subject remains in a breath-hold status, and obtain PET data of the scanning area of the subject. The PET data may correspond to a respiration signal with a plurality of respiratory phases of the subject. The respiratory phases may include a first respiratory phase and a second respiratory phase. The system may be also directed to gate the PET data into a plurality of bins based on the plurality of respiratory phases of the respiration signal, and reconstruct a plurality of gated PET images corresponding to the plurality of respiratory phases based on the gated PET data. The plurality of gated PET images may include a first gated PET image corresponding to the first respiratory phase and a second gated PET image corresponding to the second respiratory phase. The system may further be directed to determine a first motion vector field between the first gated PET image and the second gated PET image, determine a second motion vector field between the anatomical image and the second gated PET image based on the first motion vector field, and reconstruct an attenuation corrected PET image based on the PET data, the second motion vector field, and the anatomical image.

According to another aspect of the present disclosure, a non-transitory storage medium may include a set of instructions. When executed by at least one processor of a system, the set of instructions may cause the system to perform a method. The method may include obtaining an anatomical image of a scanning area of a subject acquired when the subject remains in a breath-hold status, and obtaining PET data of the scanning area of the subject. The PET data may correspond to a respiration signal with a plurality of respiratory phases of the subject, the respiratory phases including a first respiratory phase and a second respiratory phase. The method may also include gating the PET data into a plurality of bins based on the plurality of respiratory phases of the respiration signal, and reconstructing a plurality of gated PET images corresponding to the plurality of respiratory phases based on the gated PET data. The plurality of gated PET images may include a first gated PET image corresponding to the first respiratory phase and a second gated PET image corresponding to the second respiratory phase. The method may further include determining a first motion vector field between the first gated PET image and the second gated PET image, and determining a second motion vector field between the anatomical image and the second gated PET image based on the first motion vector field. The method may further include reconstructing an attenuation corrected PET image based on the PET data, the second motion vector field, and the anatomical image.

According to another aspect of the present disclosure, a system having at least one processor and storage may include an acquisition module and a processing module. The acquisition module may be configured to obtain an anatomical image of a scanning area of a subject acquired when the subject remains in a breath-hold status, and obtain PET data of the scanning area of the subject. The PET data may correspond to a respiration signal with a plurality of respiratory phases of the subject. The respiratory phases may include a first respiratory phase and a second respiratory phase. The processing module may include a gating unit, a reconstruction unit, and a motion vector field determination unit. The gating unit may be configured to gate the PET data into a plurality of bins based on the plurality of respiratory phases of the respiration signal. The reconstruction unit may be configured to reconstruct a plurality of gated PET images corresponding to the plurality of respiratory phases based on the gated PET data. The plurality of gated PET images may include a first gated PET image corresponding to the first respiratory phase and a second gated PET image corresponding to the second respiratory phase. The motion vector field determination unit may be configured to determine a first motion vector field between the first gated PET image and the second gated PET image, and determine a second motion vector field between the anatomical image and the second gated PET image. The reconstruction unit may be further configured to reconstruct an attenuation corrected PET image based on the PET data, the second motion vector field, and the anatomical image.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 6 is a flowchart illustrating an exemplary process for reconstructing an attenuation corrected PET image according to some embodiments of the present disclosure;

FIG. 8 is a flowchart illustrating an exemplary process for gating PET data according to some embodiments of the present disclosure;

FIG. 9 is a flowchart illustrating an exemplary process for determining a motion vector field between a gated PET image and a CT image according to some embodiments of the present disclosure;

DETAILED DESCRIPTION

Figure 1:
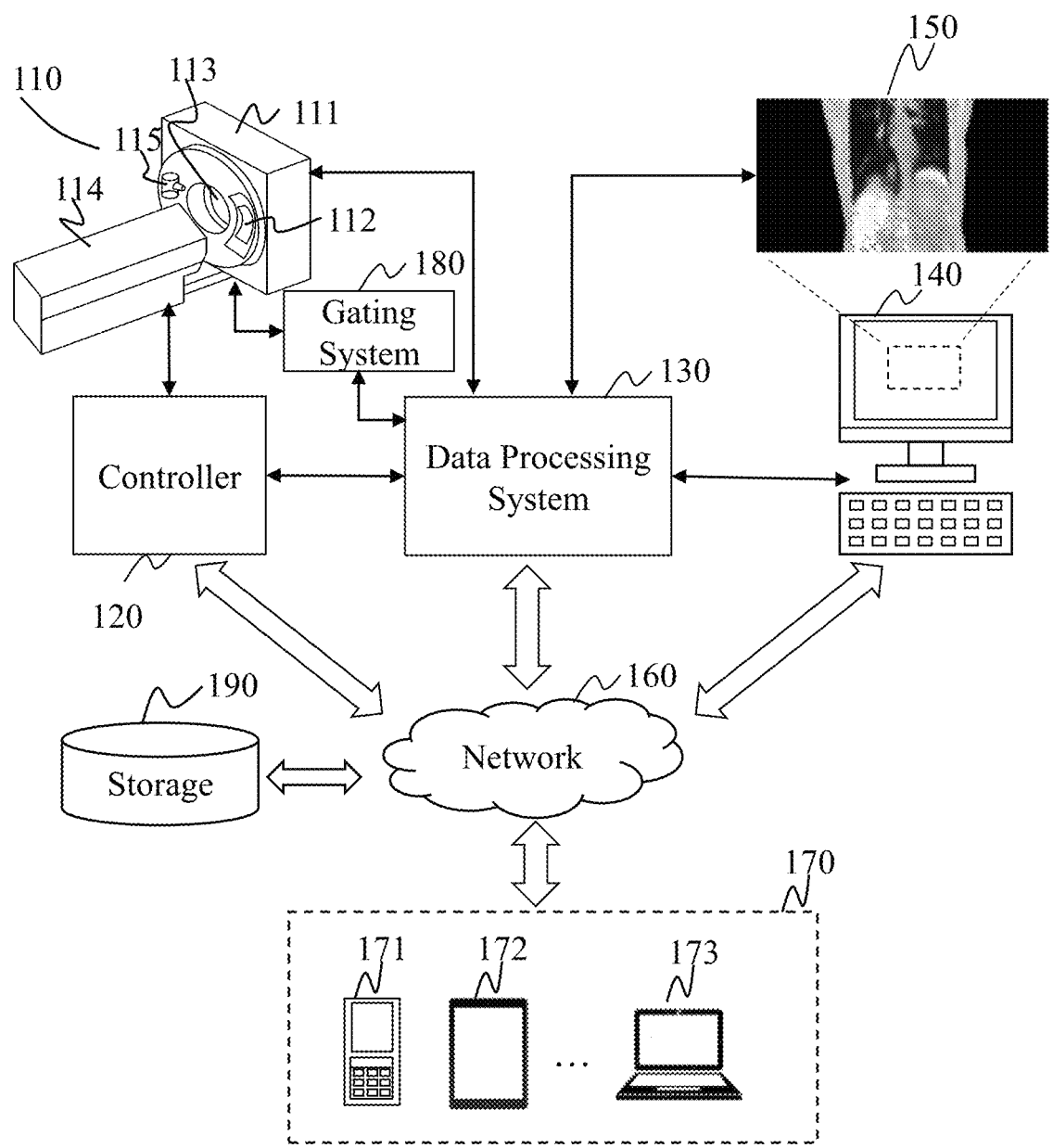
FIG. 1 is a schematic diagram illustrating an exemplary imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an erasable programmable read-only memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for non-invasive imaging, such as for disease diagnosis or research purposes. In some embodiments, the imaging system may be a computed tomography (CT) system, a magnetic resonance imaging (MRI) system, a positron emission tomography (PET) system, a PET-CT system, a PET-MRI system, or the like, or any combination thereof.

The following description is provided to help better understanding PET/CT image reconstruction methods and/or systems. The term "image" used in this disclosure may refer to a 2D image, a 3D image, a 4D image, and/or any related image data (e.g., CT data, projection data corresponding to the CT data). This is not intended to limit the scope the present disclosure. For persons having ordinary skills in the art, a certain amount of variations, changes, and/or modifications may be deducted under the guidance of the present disclosure. Those variations, changes, and/or modifications do not depart from the scope of the present disclosure.

The present disclosure relates to systems and methods for reconstructing an attenuation corrected PET image. The systems and methods may reconstruct the attenuation corrected PET image based on PET data acquired when the scanned subject in a breathing status and an anatomical image acquired when the subject remains in a breath-hold status (e.g., a deep inspiration breath-hold status, a deep expiratory breath-hold status). The anatomical image may include a CT image or an MR image. For illustration purposes, the reconstruction of an attenuation corrected PET image based on the CT image is described as an example in the present disclosure. The PET data and the CT image may correspond to a same scanning area of the subject. The PET data may be gated to reconstruct a plurality of gated PET images corresponding to the plurality of respiratory phases. The gated PET images may include a gated PET image corresponding to an end-expiratory phase and a gated PET image corresponding to an end-inspiratory phase. A PET motion vector field between the gated PET images corresponding to the end-inspiratory phase and the end-expiratory phase may be determined. A PET-CT motion vector field between a gated PET image corresponding to the end-inspiratory phase or the end-expiratory phase and the CT image may be determined based on the PET motion vector field. An attenuation corrected PET image may then be reconstructed based on the PET data (or gated PET data), the CT image, and the PET-CT motion vector field.

The attenuation corrected PET image may refer to a PET image (or a gated PET image) that is attenuation corrected based on a CT image (or a corrected CT image). The attenuation corrected PET image may include an attenuation corrected gated PET image, an attenuation corrected reference PET image, an attenuation corrected average PET image, or the like. The attenuation corrected gated PET image may refer to a PET image corresponding to a certain respiratory phase. The attenuation corrected gated PET image may be generated based on the gated PET data and a CT image (or corrected CT image corresponding to the respiratory phase). The attenuation corrected reference PET image (also referred to as a reference PET image for brevity) may refer to a PET image corresponding to a reference respiratory phase among a plurality of respiratory phases. The attenuation corrected average PET image (also referred to as an average PET image for brevity) may refer to a PET image corresponding to the average of a plurality of respiratory phases. The reference PET image and/or the average PET image may be generated based on a plurality of attenuation corrected gated PET images.

FIG. 1 illustrates an exemplary imaging system 100 according to some embodiments of the present disclosure. An imaging system 100 may produce an image of a subject. As illustrated, the imaging system 100 may include an imaging device 110, a controller 120, a data processing system 130, an input/output device 140, a network 160, and a terminal(s) 170, a gating system 180, storage 190.

In some embodiments, the imaging device 110 may scan a subject, and acquire data relating to the subject. In some embodiments, the imaging device 110 may be, for example, a PET device, a CT device, an MRI device, or the like, or any combination thereof (e.g., a PET-CT device, a PET-MRI device, or a CT-MRI device). In some embodiments, the imaging device 110 may be a radiation imaging device. The radiation imaging device may include a radiation source to emit radioactive rays to the subject to be scanned. The radioactive rays may include, for example, particle rays, photon rays, or the like, or any combination thereof. The particle rays may include neutrons, protons, electrons, μ-mesons, heavy ions, or the like, or any combination thereof. The photon rays may include X-ray, γ-ray, α-ray, β-ray, ultraviolet, laser, or the like, or any combination thereof.

In some embodiments, the imaging device 110 may be a PET/CT imaging device including a gantry 111, a detector 112, a detection region 113, a table 114, and a radiation source 115. The gantry 111 may support the detector 112 and the radiation source 115. A subject may be placed on the table 114 for scanning. The radiation source 115 may emit radioactive rays to the subject. The detector 112 may detect radiation events (e.g., gamma photons) emitted from the detection region 113. In some embodiments, the detector 112 may include one or more detector units. The detector 112 may include a scintillation detector (e.g., a cesium iodide detector), a gas detector, etc. The detector 112 may be and/or include a single-row detector in which a plurality of detector units are arranged in a single row and/or a multi-row detector in which a plurality of detector units are arranged in multiple rows.

The controller 120 may control the imaging device 110, the input/output device 140, and/or the data processing system 130. In some embodiments, the controller 120 may control the X-ray generation unit and/or the X-ray detection unit (if any) of the imaging device 110. The controller 120 may receive information from or send information to the imaging device 110, the input/output device 140, and/or the data processing system 130. For example, the controller 120 may receive commands from the input/output device 140 provided by a user. As another example, the controller 130 may process data input by a user via the input/output unit 140 and transform the data into one or more commands. As a further example, the controller 120 may control the imaging device 110, the input/output device 140, and/or the data processing system 130 according to the received commands or transformed commands. As still a further example, the controller 120 may receive image signals or data related to a subject from the imaging device 110. As still a further example, the controller 120 may send image signals or data to the data processing system 130. As still a further example, the controller 120 may receive processed data or a reconstructed image from the data processing system 130. As still a further example, the controller 120 may send processed data or a reconstructed image to the input/output device 140 for displaying. In some embodiments, the controller 120 may include a computer, a program, an algorithm, software, a storage device, one or more interfaces, etc. Exemplary interfaces may include the interfaces with the imaging device 110, the input/output device 140, the data processing system 130, and/or other modules or units in the imaging system 100.

In some embodiments, the controller 120 may receive a command provided by a user including, for example, an imaging technician, a doctor, etc. Exemplary commands may relate to a scan time, a location of the subject, the location of a table on which the subject lies, a rotation speed of the gantry, a specific parameter relating to a threshold that may be used in the image reconstruction process, or the like, or any combination thereof. In some embodiments, the controller 120 may control the data processing system 130 to select different algorithms to process the raw data of an image.

The data processing system 130 may process information received from the imaging device 110, the controller 120, the input/output device 140, and/or the terminal 170. In some embodiments, the data processing system 130 may reconstruct a CT image and/or a PET image based on the information acquired by the imaging device 110. The data processing system 130 may deliver the images to the input/output device 140 for display. In some embodiments, the data processing system 130 may perform operations including, for example, data preprocessing, image reconstruction, image correction, image composition, lookup table creation, or the like, or any combination thereof. In some embodiments, the data processing system 130 may process data based on an algorithm including, for example, the Fourier slice theorem, a filtered back projection algorithm, fan-beam reconstruction, iterative reconstruction, or the like, or any combination thereof. Merely by way of example, image data regarding a lung may be processed in the data processing system 130. In some embodiments, the data processing system 130 may generate a reconstructed PET image based on a CT image. In some embodiments, artifacts may appear in the PET image because of a mismatch of the PET data of a subject in a breathing status and CT data of the subject in the breath-hold status. The data processing system 130 may apply various algorithms or techniques to reduce the artifacts. For example, the projection data relating to the chest of the object may be processed to reduce the artifacts.

In some embodiments, the data processing system 130 may generate a control signal relating to the configuration of the imaging device 110. In some embodiments, the result generated by the data processing system 130 may be provided to other modules or units in the system including, e.g., a database 190, a terminal 170 via the network 160.

The input/output device 140 may receive or output information. In some embodiments, the input/output device 140 may include a keyboard, a touch screen, a mouse, a remote controller, or the like, or any combination thereof. The input and/or output information may take the form of a program, software, an algorithm, data, text, a number, an image, voice, or the like, or any combination thereof. For example, a user may input some initial parameters or conditions to initiate an imaging process. As another example, some information may be imported from an external resource including, for example, a floppy disk, a hard disk, a wired terminal, a wireless terminal, or the like, or any combination thereof. The output information may be transmitted to a display device, a printer, a storage device, a computing device, or the like, or a combination thereof. In some embodiments, the input/output device 140 may include a graphical user interface. The graphical user interface may facilitate a user to input parameters, and/or intervene in a data processing procedure.

The network 160 may include any suitable network that can facilitate the exchange of information and/or data for the imaging system 100. In some embodiments, one or more components of the imaging system 100 (e.g., the imaging device 110, the controller 120, the data processing system 130, the input/output device 140, and/or the terminal 170, etc.) may communicate information and/or data with one or more other components of the imaging system 100 via the network 160. For example, the data processing system 130 may obtain image data from the imaging device 110 via the network 160. As another example, the data processing system 130 may obtain user instructions from the terminal 170 via the network 160.

The network 160 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 160 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 160 may include one or more network access points. For example, the network 160 may include wired and/or wireless network access points such as base stations and/or internet exchange points through which one or more components of the imaging system 100 may be connected to the network 160 to exchange data and/or information.

The terminal(s) 170 may include a mobile device 171, a tablet computer 172, a laptop computer 173, or the like, or any combination thereof. In some embodiments, the mobile device 171 may include a smart home device, a wearable device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, a smart accessory, or the like, or any combination thereof. In some embodiments, the mobile device 171 may include a mobile phone, a personal digital assistant (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality device, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 170 may be part of or communicate with the data processing system 130.

The gating system 180 may collect information relating to, for example, breathing, heartbeat, etc. The gating system 180 may analyze the information to obtain a motion signal including, for example, a respiration signal, a cardiac motion signal, etc. The gating system 180 may include a gating camera for detecting a motion of the subject, a control panel, a marker on a surface of the subject for indicating a motion of the subject, or the like, or any combination thereof. In some embodiments, the gating camera may be an infrared camera. For example, when the imaging device 110 is scanning a patient, the gating system may be triggered automatically. The gating system 180 may collect information associated with the respiration motion of the subject during the scanning. The data collected by the gating system 180 may be stored together with the PET data or CT data.

In some embodiments, the imaging device 110, the controller 120, the data processing system 130, the input/output device 140, the terminal 170, and the gating system 180 may be connected to or communicate with each other directly. In some embodiments, the imaging device 110, the controller 120, the data processing system 130, the input/output device 140 may be connected to or communicate with each other via a network 160. In some embodiments, the imaging device 110, the controller 120, the data processing system 130, the input/output device 140 may be connected to or communicate with each other via an intermediate unit (not shown in FIG. 1). The intermediate unit may be a visible component or an invisible field (radio, optical, sonic, electromagnetic induction, etc.). The connection between different units may be wired or wireless. The wired connection may include using a metal cable, an optical cable, a hybrid cable, an interface, or the like, or any combination thereof. The wireless connection may include using a Local Area Network (LAN), a Wide Area Network (WAN), a Bluetooth, a ZigBee, a Near Field Communication (NFC), or the like, or any combination thereof. The network 160 may be used in connection with the present system described herein are not exhaustive and are not limiting.

The storage 190 may store information related to the imaging system 100. In some embodiments, the storage 190 may perform some storage-related function, such as data consolidation and/or data pre-processing. The storage 190 may acquire information from or output information to other modules. The information stored in storage 190 may be acquired from or output to an external resource, such as a floppy disk, a hard disk, a CD-ROM, a network server, a cloud server, a wireless terminal, or the like, or any combination thereof.

The storage 190 may store information by way of electric, magnetic, optical energy, or virtual storage resources, etc. The storage module that stores information by way of electric energy may include Random Access Memory (RAM), Read Only Memory (ROM), flash memory, or the like, or any combination thereof. The storage module that stores information by way of magnetic energy may include a hard disk, a floppy disk, a magnetic tape, a magnetic core memory, a bubble memory, a USB flash drive, or the like, or any combination thereof. The storage module that stores information by way of optical energy may include CD (Compact Disk), VCD (Video Compact Disk), or the like, or any combination thereof. The storage module that stores information by way of virtual storage resources may include cloud storage, a virtual private network, and/or other virtual storage resources. The method to store information may include sequential storage, link storage, hash storage, index storage, or the like, or any combination thereof.

It should be noted that the above description of the imaging system 100 is merely an example, and should not be understood as the only embodiment. To those skilled in the art, after understanding the basic principles of the connection between different units, the units and connection between the units may be modified or varied without departing from the principles. The modifications and variations are still within the scope of the current application described above. In some embodiments, these units may be independent, and in some embodiments, part of the units may be integrated into one unit to work together. In some embodiments, the imaging device 110 may be used in internal inspection of components including e.g., flaw detection, security scanning, failure analysis, metrology, assembly analysis, void analysis, wall thickness analysis, or the like, or any combination thereof.

Figure 2:
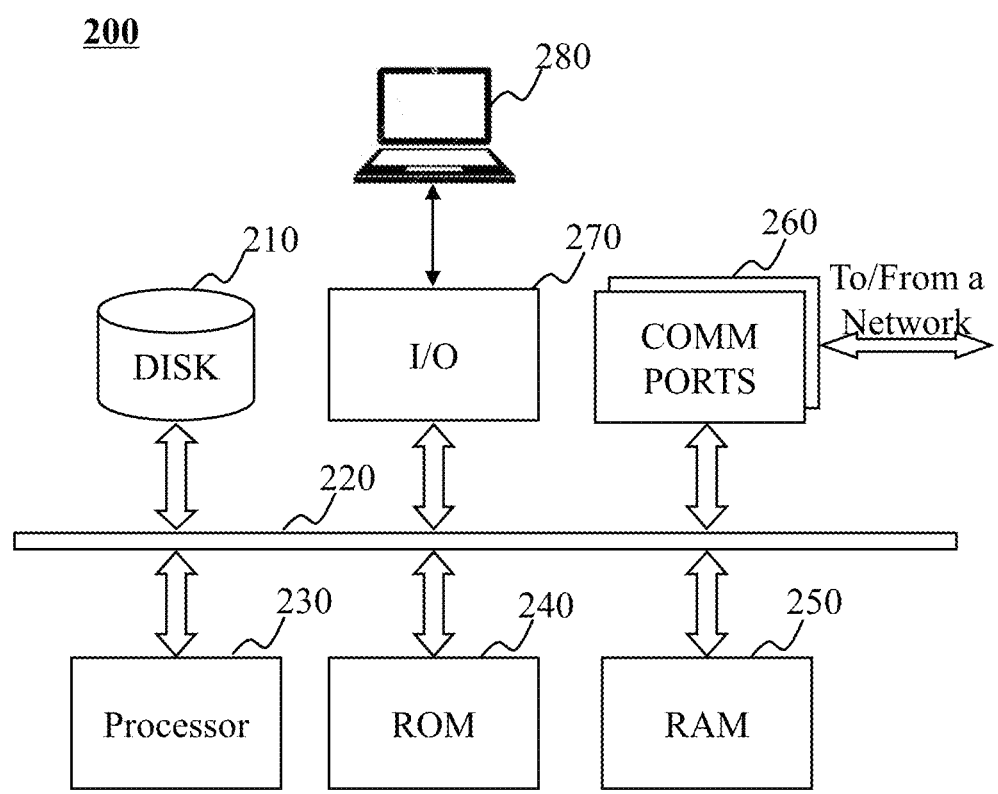
FIG. 2 is a schematic diagram illustrating exemplary hardware and software components of a computing device on which data processing system or a portion thereof may be implemented according to some embodiments of the present disclosure.

FIG. 2 is a schematic diagram illustrating exemplary hardware and software components of a computing device 200 on which data processing system 130 or a portion thereof may be implemented according to some embodiments of the present disclosure. For example, the processing module 440 may be implemented on the computing device 200 and configured to perform functions of the data processing system 130 described in this disclosure.

The computing device 200 may be a general-purpose computer or a special purpose computer, both may be used to implement an on-demand system for the present disclosure. The computing device 200 may be used to implement any component of the on-demand service as described herein. For example, the data processing system 130 may be implemented on the computing device 200, via its hardware, software program, firmware, or any combination thereof. Although only one such computer is shown, for convenience, the computer functions relating to the on-demand service as described herein may be implemented in a distributed fashion on a number of similar platforms, to distribute the processing load.

The computing device 200, for example, may include communication (COMM) ports 260 connected to and from a network to facilitate data communications. The computing device 200 may also include a processor 230 (e.g., a central processing unit (CPU)), in the form of one or more processors, for executing program instructions. The exemplary computer platform may include an internal communication bus 220, program storage and data storage of different forms, for example, a disk 210, and a read only memory (ROM) 240, or a random-access memory (RAM) 250, for various data files to be processed and/or transmitted by the computer. The exemplary computer platform may also include program instructions stored in the ROM 240, RAM 250, and/or another type of non-transitory storage medium to be executed by the processor 230. The methods and/or processes of the present disclosure may be implemented as the program instructions. The computing device 200 also includes an I/O component 270, supporting input/output between the computer and other components therein such as user interface elements 280. The computing device 200 may also receive programming and data via network communications.

Merely for illustration, only one processor is illustrated in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two different processors jointly or separately in the computing device 200 (e.g., the first processor executes operation A and the second processor executes operation B, or the first and second processors jointly execute operations A and B).

Figure 3:
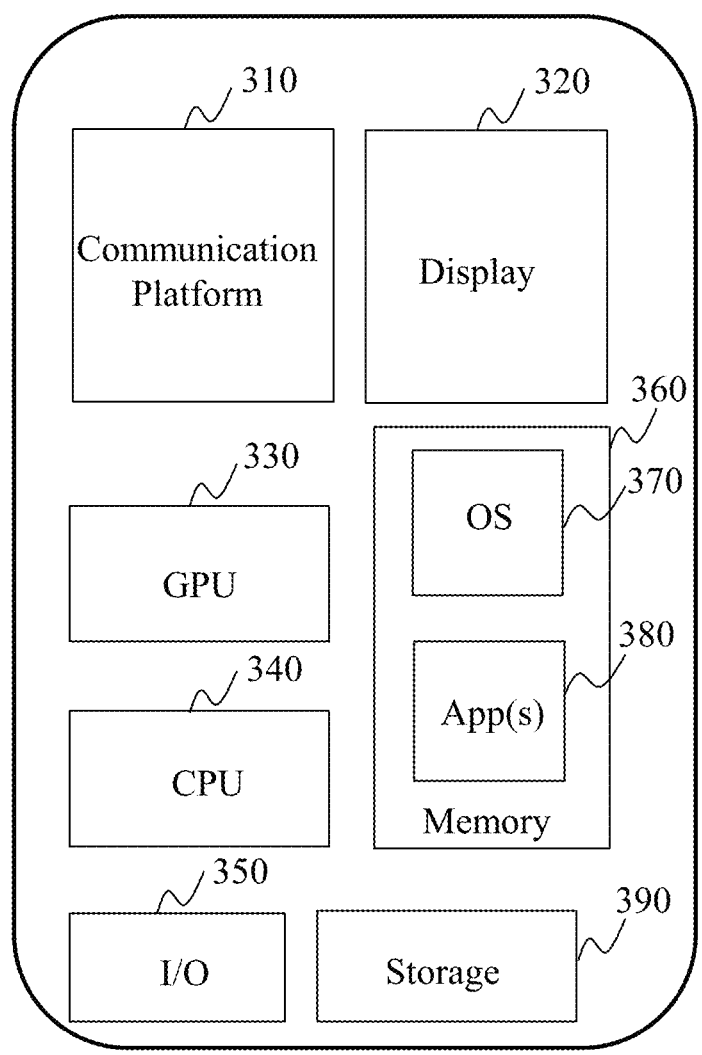
FIG. 3 is a schematic diagram illustrating exemplary hardware and/or software components of a mobile device on which a use terminal may be implemented according to some embodiments of the present disclosure.

FIG. 3 is a schematic diagram illustrating exemplary hardware and/or software components of an exemplary mobile device 300 on which a terminal 170 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, an operation system (OS) 370, applications 380, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to image processing or other information from the data processing system 130. User interactions with the information stream may be achieved via the I/O 350 and provided to the data processing system 130 and/or other components of the imaging system 100 via the network 160.

Figure 4:
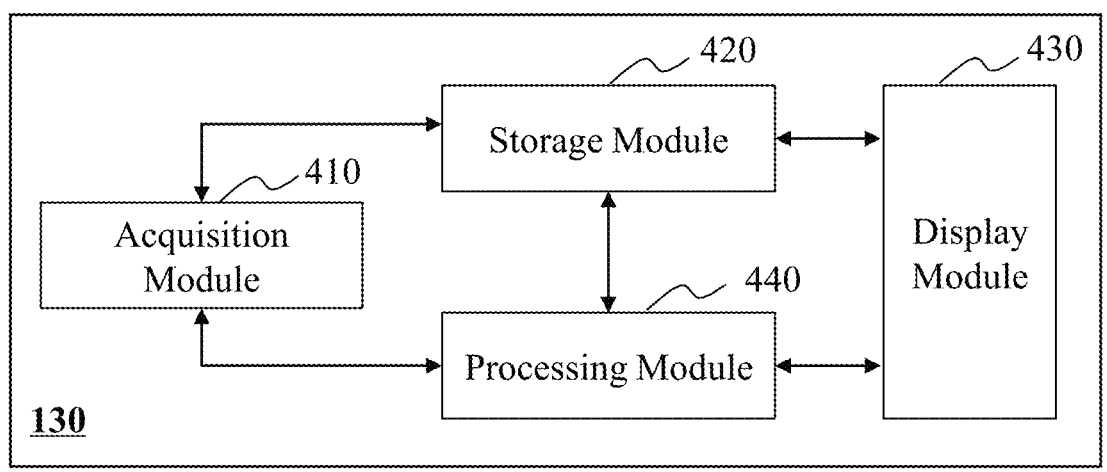
FIG. 4 is a block diagram illustrating an exemplary data processing system according to some embodiments of the present disclosure.

FIG. 4 is a block diagram illustrating an exemplary data processing system 130 according to some embodiments of the present disclosure. As shown in FIG. 4, the data processing system 130 may include a data acquisition module 410, a storage module 420, a display module 430, and a processing module 440. At least a portion of the data processing system 130 may be implemented on the computing device 200 as illustrated in FIG. 2, or the mobile device 300 as illustrated in FIG. 3.

The data acquisition module 410 may acquire data. The data may be acquired from one or more components of the imaging system 100, such as the imaging device 110 and/or the controller 120. In some embodiments, the data may be acquired from an external data source via the network 160. The data acquired may be 3D image data, and/or 2D image data. The data acquired may include information regarding a whole human body, a lung, a bronchus, a thorax, or the like, or any combination thereof. In some embodiments, the data acquisition module 410 may include a wireless receiver to receive data via the network 160.

The storage module 420 may store data. The data stored may be a numerical value, a signal, an image, information of a subject, an instruction, an algorithm, or the like, or a combination thereof. The data stored may be acquired by the data acquisition module 410, imported via the input/output device 140, generated in the processing module 440, or pre-stored in the storage module 420 during system initialization or before an operation of data processing. The storage module 420 may include a system storage device (e.g., a disk) that is provided integrally (i.e. substantially non-removable), or a storage device that is removable connectable to the system via, for example, a port (e.g., a UBS port, a firewire port, etc.), a drive (a disk drive, etc.), etc. The storage module 420 may include, for example, a hard disk, a floppy disk, selectron storage, random access memory (RAM), dynamic random access memory (DRAM), static random access memory (SRAM), bubble memory, thin film memory, magnetic plated wire memory, phase change memory, flash memory, a cloud disk, or the like, or a combination thereof. The storage module 420 may be connected to or communicate with one or more of the data acquisition module 410, the processing module 440, and the display module 430. In some embodiments, the storage module 420 may be operationally connected with one or more virtual storage resources (e.g., cloud storage, a virtual private network, other virtual storage resources, etc.) via the network 160.

The display module 430 may display information. The information displayed may include a value, a text, an image, and information of a subject. The information displayed may be transmitted from the data acquisition module 410, the storage module 420, and/or the processing module 440. In some embodiments, the display module 430 may transform information to the input/output device 140 for display. In some embodiments, the display module 430 may transform the image data that is generated from the processing module 440 for display. In some embodiments, the display module 430 may transform the image data directly extracted from the storage module 420 or the network 160 for display.

The processing module 440 may process data and generate an image. The data may be acquired from the data acquisition module 410, the storage module 420, etc. The image may be transmitted by the processing module 440 to the display module 430. In some embodiments, the data processed may be acquired from an external data source via the network 160. In some embodiments, the processing module 440 may reconstruct image data to generate one or more images. The image data may be reconstructed by using a reconstruction algorithm. The reconstruction algorithm may be an analytic reconstruction algorithm, an iterative reconstruction algorithm, a reconstruction algorithm based on compressed sensing (CS), etc.

In some embodiments, the processing module 440 may include a universal processor, e.g., a programmable logic device (PLD), an application-specific integrated circuit (ASIC), a microprocessor, a system on chip (SoC), a digital signal processor (DSP), or the like, or any combination thereof. Two or more of these universal processors in the processing module 440 may be integrated into a hardware device, or two or more hardware devices independently with each other. It should be understood, the universal processor in the processing module 440 may be implemented via various configurations. For example, in some embodiments, the processing procedure of the processing module 440 may be implemented by hardware, software, or a combination of hardware software, not only by a hardware circuit in a programmable hardware device in an ultra large scale integrated circuit, a gate array chip, a semiconductor such as a transistor, or a field programmable gate array, a programmable logic device, and also by a software performed by various processors, and also by a combination of the hardware and the software above (e.g., firmware).

It should be noted that the above description of the data processing system 130 is merely an example, and should not be understood as the only embodiment. To those skilled in the art, after understanding the basic principles of the connection between different units, the units and connection between the units may be modified or varied without departing from the principles. The modifications and variations are still within the scope of the current application described above. For example, the display module 430 may be omitted.

Figure 5:
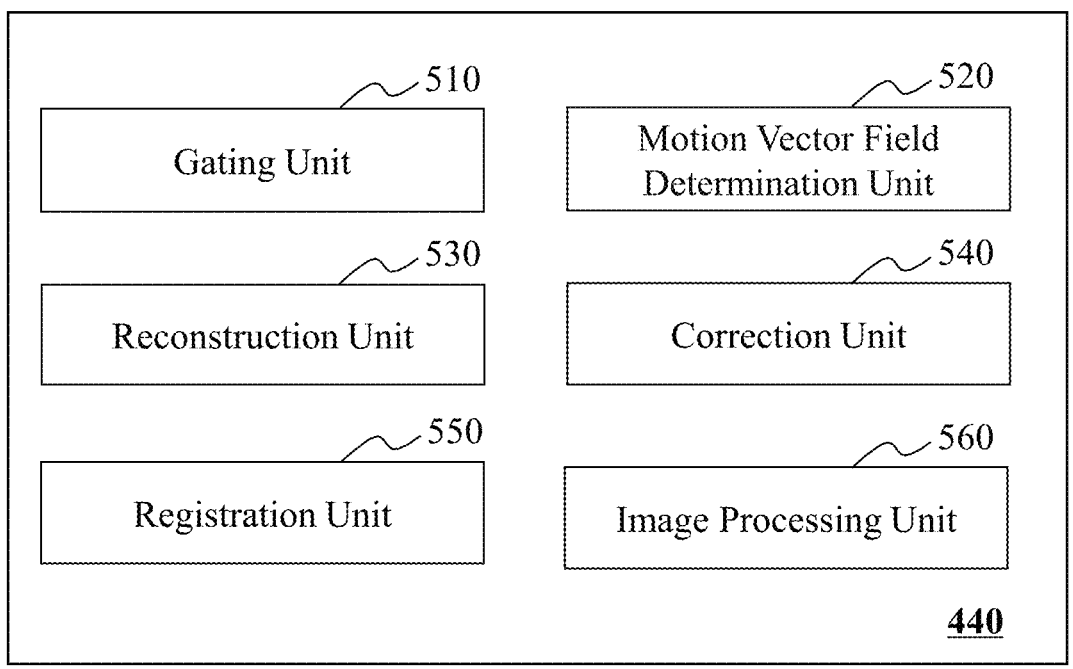
FIG. 5 is a block diagram illustrating an exemplary processing module according to some embodiments of the present disclosure.

FIG. 5 is a block diagram illustrating an exemplary processing module 440 according to some embodiments of the present disclosure. As shown in FIG. 5, the processing module 440 may include a gating unit 510, a motion vector field determination unit 520, a reconstruction unit 530, a correction unit 540, a registration unit 550, and an image processing unit 560. In some embodiments, the processing module 440 may be implemented on the processor 230 in the computing device 200, the CPU 340 in the mobile device 300, or any component of the imaging system 100. At least a portion of the processing module 440 may be implemented on the computing device 200 as illustrated in FIG. 2 or the mobile device 300 as illustrated in FIG. 3. A module may be a hardware circuit that is designed to perform one or more of the following actions, a set of instructions stored in one or more storage media, and/or any combination of the hardware circuit and the one or more storage media.

The gating unit 510 may gate (or bin) PET data into a plurality of groups or phase frames of gated PET data. The PET data may be the projection data of a PET scanning. For example, the PET data may be generated by scanning the thorax of a patient using the imaging system 100 (e.g., a PET imaging system). The PET data may be obtained from the acquisition module 410, or any other components of the imaging system 100. In some embodiments, the PET data may be transmitted or received in the form of an electronic signal. The electronic signal may be used to encode the PET data. Merely by way of example, the PET data may be retrieved from a cloud storage (e.g., a public cloud) via the network 160. In some embodiments, the PET data may be reconstructed to provide a plurality of PET images.

In some embodiments, the PET data may correspond to CT data or a CT image. For instance, the PET data and the CT data and/or CT image may be obtained by scanning a same area of a same subject (for example, a patient). The CT data may be obtained by scanning a patient before or after a PET scanning of the patient at (essentially) the same patient position. In some embodiments, the PET data of a patient may be acquired when the patient is allowed to breathe (or referred to as in the breathing status), while the corresponding CT data of the patient may be acquired when the patient remains in a breath-hold status (e.g., a deep inspiration breath-hold status, a deep expiration breath-hold status).

In some embodiments, the PET data may be gated or divided based on a gating condition. In some embodiments, the gating condition may be associated with a type of motion of the subject (or referred to as a subject motion). The subject motion may include a respiratory motion (or referred to as a respiration motion) with a plurality of respiratory phases (related description may be found elsewhere in the present disclosure), a cardiac motion with a plurality of cardiac phases, a gastrointestinal motion with a plurality of gastrointestinal phases, a skeletal muscle motion with a plurality of skeletal muscle motion phases, or the like, or any combination thereof. For example, the subject (e.g., a patient) may undergo respiratory motion during a PET scanning and/or a CT scanning. The methods and systems are described with reference to a respiratory motion for illustrated purposes, and not intended to limit the scope of the present disclosure. The systems and methods disclosed herein may be applied in the context of other motion types including, for example, cardiac motion, gastrointestinal motion, skeletal muscle motion, etc., or a combination thereof.

The gating condition may include a gating parameter, a time interval, a region of interest, a compression algorithm, or the like, or any combination thereof. The gating parameter may include a respiratory phase, a cardiac phase, a gastrointestinal phase, a skeletal muscle motion phase, or the like, or any combination thereof. The respiratory phase may correspond to the respiratory motion of the subject (e.g., the patient). The respiratory motion of the subject may include an inhaling phase (or referred to as an inspiratory phase) and/or an exhaling phase (or referred to as an expiratory phase). For example, in the inhaling phase, the patient may expand his/her chest to cause a negative pressure in the chest. The negative pressure may cause the air to flow into the lungs of the patient. As another example, in the exhaling phase, the patient may shrink the chest to cause a positive pressure in the chest. The positive pressure may push the air out of the lungs.

In some embodiments, the gating unit 510 may gate the PET data by dividing the PET data into a plurality of groups or frames based on a time interval associated with a respiratory motion. The time interval may be determined based on the amplitudes of the respiratory motion, the variation of the amplitudes with time, etc. For example, in a respiratory cycle, from an end-expiration to an end-inspiration, the motion amplitude may increase from a lowest value to a highest value. An average value of the lowest value and the highest value may be determined to be a midway amplitude. In this case, a first time interval may be determined to be the time period between the time point corresponding to an end-expiration and the time point corresponding to the midway amplitude that first appears during the respiration motion after the end-expiration. A second time interval may be determined to be the time period between the time point corresponding to the timing of the midway amplitude and the time point corresponding to the end-inspiration that first appears during the respiration motion after the midway amplitude. Similarly, the number of groups may vary, a group of PET data corresponding to a time interval that in turn corresponds to a range of respiratory motion amplitudes of the subject. In some embodiments, the time interval may be a constant.

In some embodiments, the gating unit 510 may divide the PET data based on the motion information acquired by the gating system 180. The gating system 180 may include a device for detecting a motion of the subject, a control panel, a marker on a surface of the subject for indicating a motion of the subject, or the like, or any combination thereof. In some embodiments, the gating system 180 may include a motion detection device, such as a gating camera (e.g., an infrared camera), a belt secured around the chest of the subject, or another pressure measurement technique or device to measure the change of pressure during the breathing cycles of the subject. The gating system 180 may be used to collect information relating to, for example, respiration, heartbeat, etc. The gating system 180 may analyze the information to obtain the gating parameter (e.g., the respiratory phase). In some embodiments, motion information may be derived from the imaging data including, for example, PET data. Exemplary gating techniques, including self-gating, may be found in, for example, U.S. application Ser. No. 15/386,048 filed Dec. 21, 2016 and Ser. No. 15/618,425 filed Jun. 9, 2017, both entitled "METHODS AND SYSTEMS FOR EMISSION COMPUTED TOMOGRAPHY IMAGE RECONSTRUCTION," the contents of each of which are hereby incorporated by reference.

The motion vector field determination unit 520 may determine a motion vector field between two images. In some embodiments, the motion vector field determination unit 520 may determine a PET motion vector field between two gated PET images corresponding to different respiratory phases. The motion vector field may include a plurality of motion vectors. A motion vector may be used to describe the motion of a spatial point of the subject between two respiratory phases corresponding to the two gated PET images. In some embodiments, a motion vector may be determined by registering the two gated PET images. For example, after the two gated PET images are registered, locations of two voxels in the gated PET images corresponding to a same spatial point of the subject may be determined. Then the motion vector field determination unit 520 may determine the corresponding motion vector of the spatial point based on the locations of the two voxels. A motion vector field may include a portion or all of the motion vectors between two gated PET images. The motion vector field may be used to describe a motion relationship of spatial points between two respiration phases corresponding to the two gated PET images.

In some embodiments, the motion vector field determination unit 520 may determine a motion vector field between each of the gated PET images with a reference image. The reference image may be determined by selecting one gated PET image from the plurality of gated PET images based on a selection condition (e.g., a sequence of the plurality of gated PET images). For example, a gated PET image corresponding to an end-inspiratory phase may be selected as the reference image. A gated PET image other than the reference image may be registered with the gated PET image corresponding to the end-inspiratory phase to determine a motion vector field of the gated PET image with respect to the reference image. The registration may be performed by the registration unit 550.

In some embodiments, the motion vector field determination unit 520 may determine a PET-CT motion vector field between a gated PET image and a CT image. For example, the motion vector field determination unit 520 may determine a PET-CT motion vector field between a gated PET image corresponding to an end-inspiratory phase and a CT image corresponding to a deep inspiration breath-hold status. The PET-CT motion vector field may be determined based on a motion vector field between the gated PET image corresponding to the end-inspiratory phase and a gated PET image corresponding to an end-expiratory phase. Details regarding the determination of the PET-CT motion vector field between the gated PET image and the CT image may be found elsewhere in the present disclosure. See, e.g., FIGS. 6 and 9 and the relevant descriptions thereof.

The reconstruction unit 530 may reconstruct one or more gated PET images corresponding to one or more respiratory phases. The gated PET images may be reconstructed based on the gated PET data corresponding to different respiratory phases. Additionally or alternatively, the reconstruction unit 530 may reconstruct an attenuation corrected gated PET image corresponding to a respiratory phase based on the gated PET data and a CT image (or a corrected CT image as described elsewhere in the present disclosure) corresponding to the gated PET data. In some embodiments, the attenuated corrected gated PET image may integrate information of the gated PET data and the CT image (or the corrected CT image). The anatomical information of the subject may be obtained from the CT image (or the corrected CT image), and the functional information may be obtained from the gated PET data. The reconstruction unit 530 may generate an attenuation map including a plurality of attenuation coefficients based on the CT image (or the corrected CT image). The attenuation map may be used to correct the gated PET data. The reconstruction unit 530 may then reconstruct an attenuated corrected gated PET image based on the gated PET data and the corresponding attenuation map.

In some embodiments, the reconstruction unit 530 may use a reconstruction algorithm to reconstruct a gated PET image and/or a PET image. Exemplary reconstruction algorithms may include a maximum-likelihood reconstruction of attenuation and activity (MLAA) algorithm, an iterative reconstruction algorithm (e.g., a statistical reconstruction algorithm), a Fourier slice theorem algorithm, a filtered back projection (FBP) algorithm, a compressed sensing (CS) algorithm, a fan-beam reconstruction algorithm, a maximum likelihood expectation maximization (MLEM) algorithm, an ordered subset expectation maximization (OSEM) algorithm, a maximum a posterior (MAP) algorithm, an analytic reconstruction algorithm, or the like, or any combination thereof.

The correction unit 540 may correct a CT image. In some embodiments, the correction unit 540 may correct the CT image to generate a corrected CT image corresponding to a respiratory phase based on a PET-CT motion vector field between the CT image and a gated PET image corresponding to the respiratory phase. For example, the correction unit 540 may generate a corrected CT image corresponding to an end-expiratory phase by applying a motion vector field to the CT image. The motion vector field applied to the CT image may be a motion vector field of the CT image with respect to the gated PET image corresponding to the end-expiratory phase. More descriptions regarding the correction of the CT image may be found elsewhere in the present disclosure. See, e.g., FIG. 7A and the relevant descriptions thereof.

The registration unit 550 may register two images. For example, the registration unit 550 may register two gated PET images corresponding to different motion phases (e.g., a first gated PET image corresponding to an end-expiratory phase and a second gated PET image corresponding to an end-inspiratory phase). In some embodiments, the registration unit 550 may register one or more gated PET images with a reference image. The reference image may be one of the gated PET images. Any one of the gated PET images may be designated as the reference PET image, or referred to as the reference gated PET image.

The registration may be implemented based on at least one registration algorithm. Exemplary registration algorithms may include a point-based registration algorithm (e.g., an anatomic-landmark-based registration algorithm), a curve-based registration algorithm, a surface-based registration algorithm (e.g., an surface-profile-based surface profile), a spatial alignment registration algorithm, a cross-correlation registration algorithm, a mutual-information-based registration algorithm, a sequential similarity detection algorithm (SSDA), a nonlinear transformation registration algorithm, an optical flow, demons registration algorithm, B-spline registration algorithm, or the like, or any combination thereof. In some embodiments, the registration may be performed based on a rigid transformation, an affine transformation, a projection transformation, a nonlinear transformation, an optical-flow-based registration, a similarity measurement, or the like, or any combination thereof. The similarity measurement may include a mutual-information-based measurement, a Fourier-analysis-based measurement, or the like, or any combination thereof.

The image processing unit 560 may process one or more images. In some embodiments, the image processing unit 560 may apply a motion vector field to an image (achieved according to, e.g., Equation (2)). For example, the image processing unit 560 may transform an attenuation corrected gated PET image corresponding to a respiratory phase to a phase corrected PET image corresponding to a reference respiratory phase. The phase corrected PET image may be generated by applying a PET motion vector field of the respiratory phase with respect to the reference respiratory phase to the attenuation corrected gated PET image. In some embodiments, the image processing unit 560 may sum one or more images to one image.

It should be noted that the above descriptions of the processing module 440 are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, two or more units may be integrated into one unit to perform the functions thereof. For example, the correction unit 540 may be integrated into the image processing unit 560.

FIG. 6 is a flowchart illustrating an exemplary process for reconstructing an attenuation corrected PET image according to some embodiments of the present disclosure. At least a portion of process 600 may be implemented on the computing device 200 as illustrated in FIG. 2 or the mobile device 300 as illustrated in FIG. 3. In some embodiments, one or more operations of process 600 may be implemented in the imaging system 100 illustrated in FIG. 1. For example, the process 600 may be stored in the storage module 420 of the data processing system 130 in the form of instructions, and invoked and/or executed by the data processing system 130 (e.g., the processor 230 of the data processing system 130).

In some embodiments, the attenuation corrected PET image of a subject (e.g., a patient) may be reconstructed based on CT data and PET data of the subject. The CT data may be applied in the attenuation correction of the PET data. The CT data and the PET data may need to be matched with respect to their corresponding motion phases to reduce motion artifact due to, e.g., respiratory motion, as described elsewhere in this disclosure. A CT scan usually takes a short time, and a PET scan usually takes a relatively long time. For example, a CT scan may be performed at a speed of about 1.5 seconds/table position. A PET scan may be performed at a speed of about 5 minutes/table position.

The PET data may be acquired when the subject is in a breathing status, while the CT data may be acquired when the subject remains in a breath-hold status (e.g., a deep expiration breath-hold status, a deep inspiration breath-hold status). The attenuation corrected PET image may be reconstructed based on the PET data acquired when the subject is in the breathing status and the CT data acquired when the subject remains in the deep expiration breath-hold status or the deep inspiration breath-hold status. For illustration purposes, the present disclosure takes the reconstruction of the attenuation corrected PET image based on the CT data acquired when the subject remains in the deep inspiration breath-hold status as an example.

In 610, the acquisition module 410 may obtain a CT image corresponding to a scanning area of a subject. The CT scan may be performed when the subject remains in a deep inspiration breath-hold status. When the subject remains in the deep inspiration breath-hold status, the subject may undergo no or little respiratory motion. Accordingly, the CT image may be unaffected or substantially unaffected by respiratory motion.

The CT image may be a 3D CT image including a plurality of 2D CT image layers (e.g., image slices). Alternatively, the CT image may be a 2D CT image layer (also referred to as an image slice) of a 3D CT image. In some embodiments, the CT image may be a processed CT image (e.g., an attenuation map relating to the CT image). The CT image may be generated based on CT data acquired by a CT scanner, or retrieved from a storage device via the network 160.

The subject may include a patient, an animal, a phantom, or a portion thereof including, for example, an artificial limb, an artificial heart, a tumor, any structure or organ that may be examined using X-ray, or the like, or any combination thereof. In some embodiments, the scanning area may include a whole body of the subject. Alternatively, the scanning area may be a portion of the subject, such as a brain, a lung, a liver, a kidney, a bone, any organ or region of interest (ROI) of the subject (e.g., a patient).

In 620, the acquisition module 410 may obtain PET data corresponding to the same scanning area of the subject. As used herein, a CT image and PET data (or a PET image) are considered to correspond to a same scanning area if the scanning area corresponding to the CT image at least partially overlaps with the scanning area corresponding to the PET data (or the PET image). The PET data may be acquired when the subject is in the breathing status. The PET data may correspond to the same scanning area as the CT scanning as described in connection with 610. For example, if a CT scan of a chest of the patient is performed, a PET scan of the chest of the patient may be performed when the patient keeps essentially the same patient position, in order to facilitate the combination of information of the PET data and the CT data.

During the PET data acquisition, the subject may be allowed to breathe (e.g., breathe freely). The PET data may correspond to different respiratory phases and be affected by the respiratory motion of the subject during the PET data acquisition, compared to the CT data of the same scanning area that may be acquired when the subject remains in the deep inspiration breath-hold status as described in connection with operation 610. Then the respiratory motion of the subject in the acquisition of the PET data may lead to a shift (or referred to as a mismatch) of the location of a same portion (e.g., an organ, a tissue, etc.) of the subject in the CT image with respect to the PET image or a gated PET image. For example, the location of the liver in the CT image may be different than that in the PET image or the gated PET image. When the PET image (or gated PET image) is reconstructed based on the CT image, the mismatch may reduce the image quality of the PET image (or gated PET image).

In 630, the gating unit 510 may gate (or bin) the PET data into a plurality of bins corresponding to a plurality of respiratory phases of the subject. The gated PET data may be used to reconstruct a plurality of gated PET image corresponding to the respiratory phases. The respiratory phases of the subject may include a first respiratory phase and a second respiratory phase. In some embodiments, the first respiratory phase may be an end-expiratory phase and the second respiratory phase may be an end-inspiratory phase. In some embodiments, the respiratory phases of the subject may include one or more phases between an end-expiratory phase and an end-inspiratory phase. The end-expiratory phase may refer to an end of the expiratory phase of a respiratory signal corresponding to a trough in the respiratory signal. The end-inspiratory phase may refer to an end of the inspiratory phase of the respiratory motion signal corresponding to a crest in the respiratory signal. The gated PET images may include a first gated PET image corresponding to the end-expiratory phase and a second gated PET image corresponding to the end-inspiratory phase.

In some embodiments, the gating unit 510 may gate the PET data according to a respiration signal of the subject during the PET scan. The respiration signal may be determined based on the PET data by the gating unit 510, and/or be acquired from another resource (e.g., the gating system 180). The gating unit 510 may divide the respiratory signal into a plurality of respiratory phases based on the amplitude or the time of the respiratory signal. The gating unit 510 may also determine a plurality of groups (or referred to as frames) of gated PET data corresponding to the respiratory phases. The reconstruction module 530 may reconstruct a plurality of gated PET images based on the gated PET data corresponding to the respiratory phases. More descriptions regarding the gating of the PET data and/or the reconstruction of the gated PET images may be found elsewhere in the present disclosure. See, e.g., FIG. 8 and the relevant descriptions thereof.

In 640, the registration unit 550 may register the first gated PET image corresponding the end-expiratory phase with the second gated PET image corresponding to the end-inspiratory phase. The registration unit 550 may register the two gated PET images based on a registration algorithm. Exemplary registration algorithms may include a point-based registration algorithm (e.g., an anatomic-landmark-based registration algorithm), a curve-based registration algorithm, a surface-based registration algorithm (e.g., an surface-profile-based surface profile), a spatial alignment registration algorithm, a cross-correlation registration algorithm, a mutual-information-based registration algorithm, a sequential similarity detection algorithm (SSDA), a nonlinear transformation registration algorithm, an optical flow, or the like, or any combination thereof. In some embodiments, the registration between the first and the second gated PET images may include an automatic registration, a semi-automatic registration, or a manual registration. As used herein, an automatic registration refers to a registration performed automatically by a computing device (e.g., the computing device 200 as illustrated in FIG. 2) without user intervention. As used herein, a semi-automatic registration refers to a registration performed by a computing device (e.g., the computing device 200 as illustrated in FIG. 2) with user intervention. User intervention may include providing information regarding a specific registration algorithm to be used in a registration, a parameter to be used in a registration, or the like, or a combination thereof. For instance, during a semi-automatic registration, a user provides information identifying a characteristic feature (e.g., by marking it on each of the images to be registered on a user interface displaying the images), and a computing device performs the registration based on the information in combination with a registration algorithm and/or parameter. As used herein, a manual registration refers to a registration performed according to instructions provided by a user. For example, via a user interface implemented on, e.g., an input/output device 140 or a mobile device as illustrated in FIG. 3, a user may align the two gated PET images manually to register the two gated PET images. In some embodiments, the registration may be performed based on rigid transformation, an affine transformation, a projection transformation, a nonlinear transformation, an optical-flow-based registration, a similarity measurement, or the like, or any combination thereof.

In 650, the motion vector field determination unit 520 may determine a PET motion vector field (also referred to as a first motion vector field) between the first gated PET image corresponding to the end-expiratory phase and the second gated PET image corresponding to the end-inspiratory phase based on the registration. The PET motion vector field may include a plurality of PET motion vectors. A PET motion vector may be used to describe the motion of a spatial point of the subject between the respiratory phases corresponding to the first and second gated PET images, i.e., the end-expiratory phase and the end-inspiratory phase. For example, the motion vector field determination unit 520 may determine a first location of a spatial point in the first gated PET image to be (X1, Y1, Z1), and a second location of the point in the second gated PET image to be (X2, Y2, Z2). The motion vector field determination unit 520 may further determine a PET motion vector to be (Ux, Uy, Uz) based on the first location and the second location of the spatial point, where Ux may be equal to (X1-X2), Uy may be equal to (Y1-Y2), and Uz may be equal to (Z1-Z2).

In 660, the motion vector field determination unit 520 may determine a PET-CT motion vector field (also referred to as a second motion vector field) between the second gated PET image corresponding to the end-inspiratory phase and the CT image, both corresponding to the same scanning area of the subject. The PET-CT motion vector field may be determined based on a PET motion vector field between the first gated PET image corresponding to the end-inspiratory phase and the second gated PET image corresponding to the end-expiratory phase. The PET-CT motion vector field may include a plurality of PET-CT motion vectors. A PET-CT motion vector may be used to describe the motion of a spatial point of the subject between the respiratory phases corresponding to the gated PET image and the CT image. For instance, when the CT image corresponds to the deep inspiration breath-hold status, while the gated PET image corresponds to the end-inspiratory phase, a PET-CT motion vector may be used to describe the motion of a spatial point of the subject between these two respiratory phases corresponding to the gated PET image and the CT image.

The same portion (e.g., an organ, a tissue, etc.) of the subject in the CT image corresponding to the deep inspiration breath-hold status may be different from that in any gated PET image corresponding to a respiratory phase. For example, the liver in the CT image on a coronal plane may be lower (farther away from the head of the subject) than in any gated PET image. The respiratory motion of the subject between the end-inspiratory phase and the deep inspiration breath-hold status may be similar to that between the end-expiratory phase and the end-inspiratory phase. Accordingly, the PET-CT motion vector field between the second gated PET image corresponding to the end-inspiratory phase and the CT image corresponding to deep inspiration breath-hold status may be determined based on the PET motion vector field between the first gated PET image corresponding to end-expiratory phase and the second gated PET image corresponding to the end-inspiratory phase. More descriptions regarding the determination of the PET-CT motion vector field may be found elsewhere in the present disclosure. See, e.g., FIG. 9 and the relevant descriptions thereof.

In 670, the reconstruction unit 530 may reconstruct an attenuation corrected PET image based on the CT image, the PET data (or the gated PET data), and the PET-CT motion vector field. In some embodiments, the correction unit 540 may correct the CT image to generate a corrected CT image that corresponds to the same respiratory phase as the PET data (or the gated PET data). The reconstruction unit 530 may reconstruct the attenuation corrected PET image based on the corrected CT image and the PET data (or the gated PET data).

In some embodiments, an attenuation corrected gated PET image corresponding to a respiratory phase may be generated. The correction unit 540 may generate a corrected CT image corresponding to the respiratory phase. The reconstruction unit 530 may reconstruct the attenuation corrected gated PET image corresponding to the respiratory phase based on the gated PET data and the corresponding corrected CT image. More descriptions regarding the generation of the attenuation corrected gated PET image may be found elsewhere in the present disclosure. See, e.g., FIG. 7A and the description thereof.

In some embodiments, an attenuation corrected reference PET image (also referred to as a reference PET image for brevity) corresponding to a reference respiratory phase may be generated. Any respiratory phase of the subject may be designated as the reference respiratory phase. For example, the attenuation corrected gated PET images corresponding to respiratory phases other than the reference respiratory phase may be transformed to phase corrected PET images with respect to the reference respiratory phase. The reference PET image may then be generated based on the phase corrected PET images. The reference PET image may include functional information in all respiratory phases, and thereby has a high image quality. In some embodiments, the reference PET image may further be transformed to an attenuation corrected PET image corresponding to another respiratory phase.

In some embodiments, an attenuation corrected average PET image (also referred to as an average PET image for brevity) corresponding to an average of a plurality of respiratory phases may be generated. The reconstruction unit 530 may reconstruct an attenuation corrected gated PET image corresponding to each respiratory phase by performing process 700A. The image processing unit 560 may then generate the average PET image by summing the attenuation corrected gated PET images corresponding to the plurality of respiratory phases. Alternatively, the correction unit 540 may generate a corrected CT image corresponding to each respiratory phase by performing operations 701 to 704 in the process 700A. The correction unit 540 may generate an average corrected CT image by summing the corrected CT images corresponding to the plurality of respiratory phases. The reconstruction unit 530 may then reconstruct the average PET image based on the entire (not gated) PET data and the average corrected CT image.

In some embodiments, attenuation artifacts in a PET image (e.g., a gated PET image) may be caused by attenuation of photon rays (e.g., γ rays) when they pass through the subject (e.g., a patient). The attenuation artifacts may be corrected based on an attenuation coefficient. For instance, the attenuation coefficient may be a tissue attenuation coefficient corresponding to the γ ray in an energy level of 511 KeV. The tissue attenuation coefficient may be used to determine an attenuation correction factor of the γ ray. For instance, the attenuation correction factor may be determined by Equation (1):

$$ACF = e^{\int u(x)dx},\tag{1}$$

where ACF represents the attenuation correction factor of the γ ray, and u represents the tissue attenuation coefficient.

In some embodiments, the attenuation correction factor may be determined according to a corrected CT image. For example, the attenuation correction factor of a gated PET image may be determined according to a corrected CT image corresponding to the gated PET image. The corrected CT image may be superimposed with the corresponding gated PET image so that the functional information provided by the corresponding gated PET image may be complemented by the anatomical information provided by the corrected CT image.

For example, a tissue attenuation coefficient corresponding to the X-ray may be determined based on a corrected CT image. The tissue attenuation coefficient corresponding to the X-ray may be transformed into the tissue attenuation coefficient corresponding to the γ ray, and the tissue attenuation coefficient corresponding to the γ ray may be used to determine the tissue attenuation correction factor of the γ ray using Equation (1).

In some embodiments, the reconstruction unit 530 may use a reconstruction algorithm to generate an attenuation corrected PET image (e.g., a reference PET image corresponding to a reference respiratory phase, an attenuation corrected PET image corresponding to the plurality of respiratory phase). The reconstruction algorithm may include an iterative reconstruction algorithm (e.g., a statistical reconstruction algorithm), a Fourier slice theorem algorithm, a filtered back projection (FBP) algorithm, a compressed sensing (CS) algorithm, a fan-beam reconstruction algorithm, a maximum likelihood expectation maximization (MLEM) algorithm, an ordered subset expectation maximization (OSEM) algorithm, a maximum a posterior (MAP) algorithm, an analytic reconstruction algorithm, or the like, or any combination thereof.

It should be noted that the above descriptions of the process 600 are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

In some embodiments, an attenuation corrected PET image (e.g., a reference PET image corresponding to a reference respiratory phase, an attenuation corrected average PET image corresponding to the average of the plurality of respiratory phase) may be reconstructed based on CT data acquired when the subject remains in a deep expiratory breath-hold status and the PET data acquired when the subject is in breathing status. In 610, the acquisition module 410 may obtain a CT image corresponding to a scanning area of a subject. The CT image may be acquired when the subject remains in a deep expiratory breath-hold status. In 630, the first respiratory phase may be the end-inspiratory phase and the second respiratory phase an end-expiratory phase. The PET data may be gated to reconstruct a first gated PET image corresponding to the end-inspiratory phase and a second gated PET image corresponding to the end-expiratory phase. In 660, a PET-CT motion vector field between the second gated PET image corresponding to the end-expiratory phase and the CT image corresponding to the deep expiratory breath-hold status may be determined by the motion vector field determination unit 520. In 670, an attenuation corrected PET image (e.g., a reference PET image corresponding to a reference respiratory phase, an attenuation corrected average PET image corresponding to the average of the plurality of respiratory phase) may be reconstructed based on the CT image, the PET data (or gated PET data), and the PET-CT motion vector field.

In some embodiments, the first respiratory phase and the second respiratory phase may be any two different respiratory phases in the process 600. In some embodiments, an attenuation corrected PET image may be reconstructed based on an anatomical image other than the CT image. For example, the attenuation corrected PET image may be reconstructed based on PET data and an MR image both corresponding to the same scanning area of the subject. The PET data may be acquired when the subject is in a breathing status and the MR image may be acquired when the subject remains in a deep inspiration breath-hold status or a deep expiratory breath-hold status. The MR image may provide anatomical data of the subject, which may be applied in combination with tissue attenuation coefficients of different portions in an attenuation correction of the PET data.

Figure 7A:
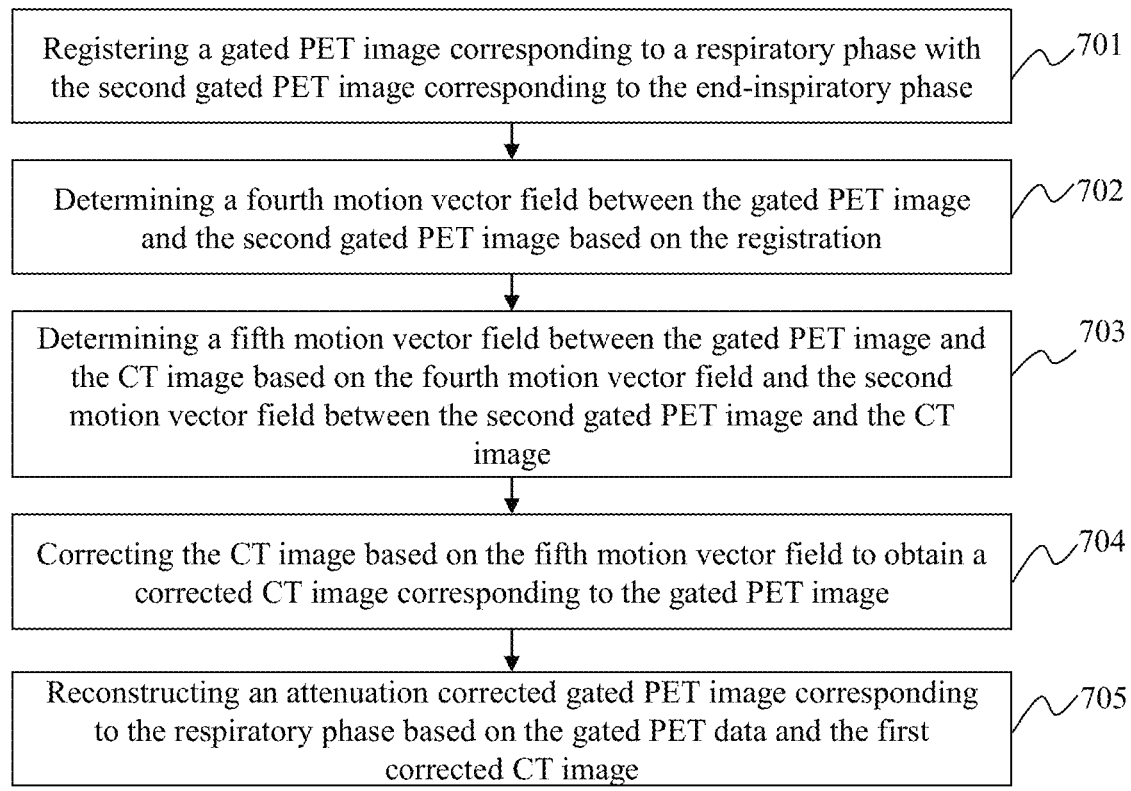
FIG. 7A is a flowchart illustrating an exemplary process for reconstructing an attenuation corrected gated PET image corresponding to a respiratory phase according to some embodiments of the present disclosure.
Figure 7B:
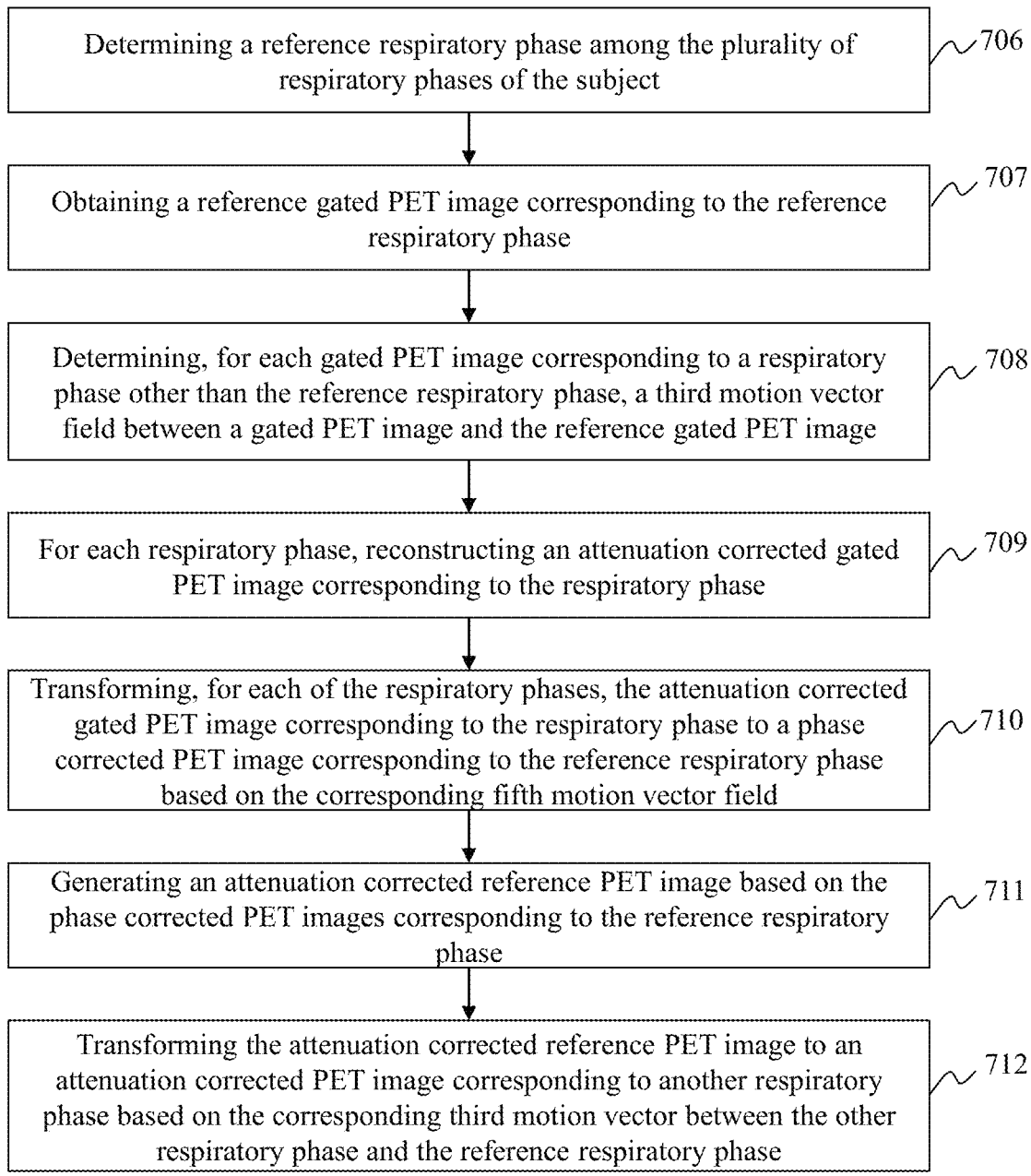
FIG. 7B is a flowchart illustrating an exemplary process for reconstructing a reference PET image corresponding to a reference respiratory phase according to some embodiments of the present disclosure.

FIG. 7A is a flowchart illustrating an exemplary process 700A for reconstructing an attenuation corrected gated PET image corresponding to a specific respiratory phase according to some embodiments of the present disclosure. FIG. 7B is a flowchart illustrating an exemplary process 700B for reconstructing a reference PET image corresponding to a reference respiratory phase according to some embodiments of the present disclosure. At least a portion of the process 700A and/or 700B may be implemented on the computing device 200 as illustrated in FIG. 2 or the mobile device 300 as illustrated in FIG. 3. In some embodiments, one or more operations of process 700A and/or 700B may be implemented in the imaging system 100 illustrated in FIG. 1. The process 700A and/or the process 700B may be performed to achieve operation 670 as described in connection with FIG. 6.

In 701, the registration unit 550 may register a gated PET image corresponding to a respiratory phase with the second gated PET image corresponding to the end-inspiratory phase. The respiratory phase may be any respiratory phase other than the end-inspiratory phase. Operation 701 may be performed in a manner similar to operation 640, and the descriptions thereof are not repeated here.

In 702, the motion vector field determination unit 520 may determine a PET motion vector field (also referred to as a fourth motion vector field) between the gated PET image and the second gated PET image corresponding to the end-inspiratory phase based on the registration between the gated PET image and the second gated PET image. Operation 702 may be performed in a similar manner with operation 650, and the descriptions thereof are not repeated here.

In 703, the motion vector field determination unit 520 may determine a PET-CT motion vector field (also referred to as a fifth motion vector field) between the gated PET image and the CT image (corresponding to the deep inspiration breath-hold status). The PET-CT motion vector field may be determined based on the PET motion vector field between the gated PET image and the second gated PET image and the PET-CT motion vector field between the second gated PET image and the CT image. For example, the motion vector field determination unit 520 may determine the PET-CT motion vector field by adding the PET motion vector field between the gated PET image and the second gated PET image and the PET-CT motion vector field between the second gated PET image and the CT image. The determination of the PET-CT motion vector field between the second gated PET image and the CT image may be found elsewhere in the present disclosure. See, e.g., FIG. 9 and the descriptions thereof.

In 704, the correction unit 540 may correct the CT image based on the PET-CT motion vector field between the gated PET image and the CT image to obtain a corrected CT image corresponding to the gated PET image. The corrected CT image corresponding to the gated PET image may have a matched respiratory phase (e.g., a same respiratory phase or a substantially same respiratory phase) with the gated PET image. The corrected CT image corresponding to the gated PET image may also be referred to as a phase-matched CT image corresponding to the gated PET image.

For illustration purposes, the PET-CT motion vector filed between the CT image and the gated PET image may be expressed as $(m_u(x, y, z), m_v(x, y, z), m_w(x, y, z))$, where $m_u$ represents the motion vector component in the x axis direction, $m_v$ represents the motion vector component in the y axis direction, $m_w$ represents the motion vector component in the z axis direction. The correction unit 540 may correct the CT image to generate the corrected CT image corresponding to the gated PET image (both relating to a same respiratory phase) by applying the PET-CT motion vector field to the CT image. The correction of the CT image may be performed according to Equation (2) below:

$$C_2(x,y,z)=C(x+m_u(x,y,z),y+m_v(x,y,z),z+m_w(x,y,z)), \quad (2)$$

where $C(x, y, z)$ represents the CT image, and $C_2(x, y, z)$ represents the corrected CT image corresponding to the gated PET image.

In 705, the reconstruction unit 530 may reconstruct an attenuation corrected gated PET image (also referred to as a first PET image) corresponding to the specific respiratory phase based on the gated PET data corresponding to the respiratory phase and the corresponding corrected CT image. The reconstruction of the attenuation corrected gated PET image may be similar to that of the PET image as described in connection with operation 670, and the descriptions thereof and are not repeated here. As described in connection with 704, the corrected CT image may have a matched respiratory phase with the gated PET image. The attenuation correction of the gated PET image based on the phase-matched CT image may also be referred to as a phase-matched attenuation correction of the gated PET image.

In some embodiments, operation 701 in the process 700 may be omitted. The PET motion vector field between a specific gated PET image and the second gated PET image corresponding to the end-inspiratory phase may be determined based on a PET motion vector field between the first gated PET image corresponding to the end-expiratory phase and the second gated PET image. For example, the PET motion vector field between the gated PET image and the second gated PET image may be determined by multiplying the PET motion vector field between the first and second gated PET images by a coefficient. The coefficient may be a default value or be adjusted according to different situations. In some embodiments, the coefficient may be associated with, such as a difference between the respiratory phase of the gated PET image and the respiratory phase of the second gated PET image. For example, the gating unit 510 may gate the PET data to four respiratory phases, that is, a mid-inspiratory phase, an end-inspiratory phase, a mid-expiratory phase, and an end-expiratory phase. The PET motion vector field between the mid-inspiratory phase and the end-inspiratory phase may be 0.5 times of the PET motion vector field between the end-inspiratory phase and the end-expiratory phase.

In some embodiments, a respiratory phase may be designated as a reference respiratory phase. The process 700A may be performed for each respiratory phase to generate a corresponding corrected CT image and reconstruct a corresponding attenuation corrected gated PET image. The process 700B may be implemented to generate a reference PET image corresponding to the reference respiratory phase based on the attenuation corrected gated PET images of the respiratory phases. The reference PET image corresponding to the reference respiratory phase may include functional information in all respiratory phases, and thereby may have a high image quality.

In 706, the gating unit 510 may determine a reference respiratory phase among the respiratory phases of the subject. Any one of the respiratory phases may be designated or referred to as the reference respiratory phase. For example, the reference respiratory phase may be an end-expiratory phase, an end-inspiratory phase, an intermediate expiratory phase, or an intermediate inspiratory phase.

In 707, the acquisition module 410 may obtain a gated PET image corresponding to the reference respiratory phase. The gated PET image corresponding to the reference respiratory phase may be referred to as a reference gated PET image. In some embodiments, the reference gated PET image may be generated by image reconstruction based on a group of gated PET data corresponding to the reference respirator phase. The reconstruction of the reference gated PET image may be performed by the reconstruction unit 530 based on a reconstruction algorithm as described elsewhere in this disclosure (e.g., FIG. 5 and the relevant descriptions). In some embodiments, in 707 a previously determined reference gated PET image may be retrieved from a storage device in the imaging system 100 (e.g., the storage 190, the storage module 420) or an external storage device via the internet 160.

In 708, for each gated PET image corresponding to a respiratory phase other than the reference respiratory phase, the motion vector field determination unit 520 may determine a PET motion vector field (e.g., also referred to as a third motion vector field) between the gated PET image and the reference gated PET image. For a gated PET image, the registration unit 550 may register the gated PET image with the reference gated PET image, and the motion vector field determination unit 520 may determine the corresponding PET motion vector field based on the registration. The registration between the gated PET image and the reference gated PET image may be similar to the registration as described in connection with operation 640, and the descriptions thereof are not repeated here. The determination of the PET motion vector field of a gated PET image with respect to the reference PET image may be similar to the determination of the PET motion vector field as described in connection with operation 650, and the descriptions thereof are not repeated here. Additionally or alternatively, the motion vector field determination unit 520 may determine the PET motion vector field between the gated PET image and the reference gated PET image based on the motion vector field between the gated PET images corresponding to the end-inspiratory phase and end-expiratory phase as described in connection with FIG. 7A.

In 709, the reconstruction unit 530 may reconstruct an attenuation corrected gated PET image corresponding to each respiratory phase. The attenuation corrected gated PET image corresponding to each respiratory phase may be reconstructed by performing the process 700A for each respiratory phase.

In 710, for each respiratory phase, the image processing unit 560 may transform the attenuation corrected gated PET image corresponding to the respiratory phase to a phase corrected PET image (also referred to as a second PET image) corresponding to the reference respiratory phase. The transformation may be performed based on the corresponding PET motion vector field of the gated PET image corresponding to the reference PET image. For example, the image processing unit 560 may apply the corresponding PET motion vector field to the attenuation corrected gated PET image corresponding to the respiratory phase to generate the phase corrected PET image. More descriptions regarding the applying a motion vector field to an image may be found elsewhere in the present disclosure. See, e.g., operation 704 and the relevant descriptions thereof.

In 711, the image processing unit 560 may generate a reference PET image corresponding to the reference respiratory phase based on plurality of phase corrected PET images corresponding to the reference respiratory phase. In some embodiments, the image processing unit 560 may generate the reference PET image corresponding to the reference respiratory phase by summing the phase corrected PET images corresponding to the reference respiratory phase. The reference PET image corresponding to the reference respiratory phase may include functional information in all respiratory phases, and thereby may have a high image quality.

In 712, the image processing unit 560 may transform the summed reference PET image corresponding to the reference respiratory phase to an attenuation corrected PET image corresponding to another respiratory phase (also be referred to as a third PET image) based on the corresponding PET motion vector field between the other respiratory phase and the reference respiratory phase. The respiratory phase may be any respiratory phase of the subject other than the reference respiratory phase. The PET motion vector field between the other respiratory phase and the reference respiratory phase may be determined in operation 708. The image processing unit 560 may apply the PET motion vector field of a certain respiratory phase corresponding to the reference respiratory phase to the reference PET image corresponding to the reference respiratory phase to generate an attenuation corrected PET image corresponding to the certain respiratory phase. The attenuation corrected PET image corresponding to the certain respiratory phase may also include functional information in all respiratory phases.

It should be noted that the above descriptions of the process 700A and/or the process 700B are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

In some embodiments, the reference PET image corresponding to the reference respiratory phase may be reconstructed based on CT data acquired when the subject remains in a deep expiratory breath-hold status and the PET data acquired when the subject is in the breathing status. The second gated PET image in the process 700 A and/or the process 700B may correspond to an end-expiratory phase. The process 700A may be performed on the second gated PET image corresponding to the end-expiratory phase to determine an attenuation corrected gated PET image corresponding to a respiratory phase. In some embodiments, the process 700A may be performed for each respiratory phase to generate a corresponding attenuation corrected gated PET image. The process 700B may be performed to generate a reference PET image corresponding to the reference respiratory phase based on the attenuation corrected gated PET images. In some embodiments, the reference PET image may be reconstructed based on an anatomical image other than the CT image. For example, the attenuation corrected PET image may be reconstructed based on PET data and an MR image both corresponding to the same scanning area of the subject. The MR image may provide anatomical data of the subject, which may be applied in combination with tissue attenuation coefficients of different portions in an attenuation correction of the PET data.

FIG. 8 is a flowchart illustrating an exemplary process for gating PET data according to some embodiments of the present disclosure. In some embodiments, at least a portion of the process 800 may be implemented on the computing device 200 as illustrated in FIG. 2 or the mobile device 300 as illustrated in FIG. 3. In some embodiments, one or more operations of process 800 may be implemented in the imaging system 100 illustrated in FIG. 1. For example, the process 800 may be stored in the storage module 420 of the data processing system 130 in the form of instructions, and invoked and/or executed by the data processing system 130 (e.g., the processor 230 of the data processing system 130). In some embodiments, the process 800 may be performed to achieve operation 630 as described in connection with FIG. 6.

In 810, the gating unit 510 may obtain a respiration signal of the subject during the PET scan. The respiration signal may correspond to a plurality of respiratory phases of the subject. In some embodiments, the gating unit 510 may obtain information of a respiratory signal relating to a respiratory motion from the PET data, and determine the respiratory signal of the respiratory motion based on the information.

In some embodiments, the respiration signal may be acquired from a source other than the PET data. For instance, the respiration signal may be obtained from the gating system 180. The gating system 180 may collect information such as breathing information, heartbeat information etc. The gating system 180 may also analyze the information to determine one or more gating parameters (e.g., the respiratory phase) and/or obtain the respiration signal.

In some embodiments, the respiratory signal may be approximated by a sine function, a cosine function, a polynomial function, a pulse function, or the like, or any combination thereof. In some embodiments, the respiratory signal may be expressed in a two-dimensional coordinate. The two-dimensional coordinate may include a first coordinate axis (or the X axis) representing time, and a second coordinate axis (or the Y axis) representing amplitude or value. For example, the respiration signal may be approximated by a sine function in the two-dimensional coordinate. The respiration signal may show the amplitude in the Y axis, and the amplitude may vary depending on the time in the X axis. In some embodiments, the respiration signal may be approximated by the sine signal or the cosine signal. The gating unit 510 may approximate the respiration signal using, for example, the sine function, the cosine function, etc. For example, the respiration signal may be approximated by Equation (3):

$$Y = c * \sin(aX + b), \quad (3)$$

where Y is the amplitude of the respiratory motion, X is the time of the respiratory motion, and a, b, and c are constant parameters.

In some embodiments, the respiratory signal may be divided into a plurality of respiratory phases. For example, the gating unit 510 may divide the respiratory signal into 4 respiratory phases, each of which may correspond to a different part in a cycle of the respiratory signal. In some embodiments, the gating unit 510 may divide the respiratory signal according to the instruction of a user (e.g., a doctor). The user may provide his/her instruction via a user interface implemented on, e.g., a mobile device as illustrated in FIG. 3.

In some embodiments, the respiratory signal may be divided according to the amplitude of the respiratory signal. For example, a cycle of the respiratory signal may be divided based on the amplitude of the respiratory signal. If the amplitude of the respiratory signal is segmented into n parts (e.g., from the maximum amplitude to the minimum amplitude), the n parts of the respiratory signal may correspond to n respiratory phases. In some embodiments, the respiratory signal may be divided, based on the time of the respiratory signal, into N parts, and the N parts may correspond to N respiratory phases. For example, if a cycle of the respiratory signal lasts 5 seconds, a cycle of the respiratory signal may be divided according to a time interval (e.g., 0.5 seconds, or 1 second), and this cycle of the respiratory signal may be divided into N respiratory phases (e.g., 5/0.5 or 10 respiratory phases, or 5/1 or 5 respiratory phases). Exemplary gating techniques, including self-gating, may be found in, for example, U.S. application Ser. No. 15/386,048 filed Dec. 21, 2016 and Ser. No. 15/618,425 filed Jun. 9, 2017, both entitled "METHODS AND SYSTEMS FOR EMISSION COMPUTED TOMOGRAPHY IMAGE RECONSTRUCTION," the contents of which are hereby incorporated by reference.

In some embodiments, the plurality of respiratory phases may include an end-expiration phrase and an end-inspiratory phase. The end-expiratory phase may refer to an end of the expiratory phase of a respiratory signal corresponding to a trough in the respiratory signal. The end-inspiratory phase may refer to an end of the inspiratory phase of the respiratory motion signal corresponding to a crest in the respiratory signal.

In 820, the gating unit 510 may gate the PET data into a plurality of bins based on the plurality of respiratory phases of the respiration signal. For example, the respiratory signal may correspond to N respiratory phases, and the gating unit 510 may gate the PET data into N groups (or frames) of gated PET data based on the N respiratory phases. Each group of gated PET data may correspond to a respiratory phase.

In 830, the reconstruction unit 530 may reconstruct a plurality of gated PET images corresponding to the respiratory phases based on the gated PET data. In some embodiments, the reconstruction unit 530 may reconstruct a gated PET image for each respiratory phase based on the corresponding group of gated PET data. Alternatively, the reconstruction unit 530 may reconstruct one or more gated PET image for a portion of respiratory phases according to different situations. In some embodiments, the reconstruction unit 530 may reconstruct a first gated PET image corresponding to the end-expiratory phase based on a group of gated PET data corresponding to the end-expiratory phase, and a second gated PET image corresponding to the end-inspiratory phase based on a group of gated PET data corresponding to the end-inspiratory phase.

In some embodiments, the reconstruction unit 530 may use a reconstruction algorithm to reconstruct a gated PET image. Exemplary reconstruction algorithms may include a maximum-likelihood reconstruction of attenuation and activity (MLAA) algorithm, an iterative reconstruction algorithm (e.g., a statistical reconstruction algorithm), a Fourier slice theorem algorithm, a filtered back projection (FBP) algorithm, a compressed sensing (CS) algorithm, a fan-beam reconstruction algorithm, a maximum likelihood expectation maximization (MLEM) algorithm, an ordered subset expectation maximization (OSEM) algorithm, a maximum a posterior (MAP) algorithm, an analytic reconstruction algorithm, or the like, or any combination thereof. In some embodiments, the reconstruction unit 530 may generate a gated PET image based on the MLAA algorithm.

In some embodiments, the reconstruction unit 530 may correct the one or more gated PET images based on one or more correction techniques. Exemplary correction techniques may include a random correction technique, a scatter correction technique, a dead time correction technique, or the like, or any combination thereof. In some embodiments, the reconstruction unit 530 may correct one or more gated PET images based on an attenuation correction technique other than a CT-based attenuation correction technique. For example, the reconstruction unit 530 may perform an attenuation correction of the one or more gated PET images based on an MLAA algorithm.

FIG. 9 is a flowchart illustrating an exemplary process for determining a motion vector field between a gated PET image and a CT image according to some embodiments of the present disclosure. In some embodiments, process 900 may be performed to achieve operation 660 as described in connection with FIG. 6. In some embodiments, at least a portion of the process 900 may be implemented on the computing device 200 as illustrated in FIG. 2 or the mobile device 300 as illustrated in FIG. 3. In some embodiments, one or more operations of process 900 may be implemented in the imaging system 100 illustrated in FIG. 1. For example, the process 900 may be stored in the storage module 420 of the data processing system 130 in the form of instructions, and invoked and/or executed by the data processing system 130 (e.g., the processor 230 of the data processing system 130).

In 910, the motion vector field determination unit 520 may determine a plurality of candidate CT images based on the CT image and the PET motion vector field between the first gated PET image and the second gated PET image (also referred to as a first motion vector field). As described in connection with FIG. 6, an attenuation corrected PET image of a subject may be generated based on PET data acquired when the subject is in the breathing status and the CT data acquired when the subject remains in a deep expiration breath-hold status or a deep inspiration breath-hold status. When the CT data is acquired when the subject remains in a deep expiration breath-hold status, the first gated PET image may correspond to an end-expiratory phase and the second gated PET image may correspond to an end-expiratory phase. When the CT data is acquired when the subject remains in a deep inspiration breath-hold status, the first gated PET image may correspond to the end-expiratory phase and the second gated PET image may correspond to an end-inspiratory phase. For illustration purposes, the determination of a PET-CT motion vector field between the second gated PET image corresponding to the end-inspiratory phase and the CT image corresponding to the deep inspiration breath-hold status is described as an example in the present disclosure.

In some embodiments, the motion vector field determination unit 520 may generate a candidate CT image by applying a motion vector field to the CT image. The motion vector field applied to the CT may be a times of the PET motion vector field between the gated PET image corresponding to the end-expiratory phase and the gated PET image corresponding to the end-inspiratory phase. The $\alpha$ is a coefficient, and may have any value. The candidate CT image may be determined according to Equation (4) as below:

$$C'(x)=C(x+\alpha T_{1\to 2}) \qquad (4)$$

where C'(x) represents the candidate CT image, C(x) represents the CT image, x represents the coordinates of a pixel in a 2D candidate CT image or a voxel in a 3D candidate CT image, $T_{1\to 2}$ represents the PET motion vector field between the first gated PET image (corresponding to the end-expiratory phase) and the second gated PET image (corresponding to the end-inspiratory phase), and $\alpha T_{1\to 2}$ represents a motion vector field that is $\alpha$ times of $T_{1\to 2}$.

In some embodiments, the motion vector field determination unit 520 may determine the plurality of candidate CT images according to different values of $\alpha$.

In 920, the motion vector field determination unit 520 may determine a similarity between the second gated PET image (corresponding to the end-inspiratory phase) and one or more of the candidate CT images generated in 920. In some embodiments, the similarity may include a pixel-based similarity, an entropy-based similarity, a mutual information similarity, or the like, or any combination thereof. In some embodiments, the motion deformation determination unit 520 may determine the mutual information similarity between a candidate CT image and the second gated PET image based on Equation (5):

$$D(P_2, C')=H(P_2)+H(C')-H(P_2,C'), \qquad (5)$$

where, D(P$_2$, C') represents mutual information between the second gated PET image and the candidate CT image, H(P$_2$) represents an entropy of the second gated PET image, H(C') represents an entropy of the candidate CT image, and H(P$_2$, C') represents a joint entropy of the second gated PET image and the candidate CT image. When the second gated PET image and the candidate CT image are irrelevant, the joint entropy may be substantially similar to a sum of the entropies of the two images. When the second gated PET image and the candidate CT image are relevant, the joint entropy may be closer to the larger entropy of the two images, the second gated PET image and the candidate CT image. In some embodiments, the entropy of the second gated PET image H(P$_2$), or the entropy of the candidate CT image H(C') may be determined by Equation (6):

$$H(A)=-\int_0^{+\infty} p_A(v)\log(p_A(v))dv, \qquad (6)$$

where $p_A(v)$ represent a histogram of the image A. The image A may be the second gated PET image or the candidate CT image. In some embodiments, $p_A(v)$ of the image A is determined by Equation (7):

$$p_A(v)=\iint_{All}\delta((A(x,y)-v)dxdy, \qquad (7)$$

where A(x,y) represents a pixel value of a pixel at (x,y) in the image A, v is a gray value, $\delta$ represents a window function centered at 0 (e.g., a Gaussian function with mean 0).

In some embodiments, the joint entropy H(P$_2$,C') of the candidate CT image and the second gated PET image may be determined by Equation (8):

$$H(P_2,C')=-\iint_0^{+\infty} p_{P_2,C'}(v,u)\log(p_{P_2,C'}(v,u))dudv, \qquad (8)$$

where u represents a pixel value of a pixel in the second gated PET image, v represents a pixel value of a corresponding pixel in the candidate CT image, and $p_{P_c,C}(v,u)$ is a pixel value of combined histogram of the corresponding pixel of the second gated PET image and the candidate CT image. In some embodiments, $p_{P_c,C}(v,u)$ may be determined by Equation (9):

$$p_{P_c,C}(v,u)=\iint_{CB}\delta(P_2(x,v)-v)\delta(C'(x,y)-u)dxdy, \qquad (9)$$

where $\delta$ represents a window function centered at 0. In some embodiments, the function $\delta$ in Equation (7) and Equation (9) may take the form of the Dirac delta function, as determined by Equations (10) and (11):

$$\delta(x) = \begin{cases} +\infty, & x=0 \\ 0, & x \neq 0' \end{cases} \qquad (10)$$

which is constrained to satisfy the identity:

$$\int_{-\infty}^{+\infty}\delta(x)dx=1. \qquad (11)$$

In 930, the motion vector field determination unit 520 may identity a highest similarity among the determined similarities. In some embodiments, the motion vector field determination unit 520 may rank the similarities, e.g., from the lowest similarity to the highest similarity, or vice versa, and identify the highest similarity.

In 940, the motion vector field determination unit 520 may determine the PET-CT motion vector field between the second gated PET image and the CT image based on the identified highest similarity. The motion vector field determination unit 520 may determine the candidate CT image corresponding to the highest similarity (having a highest similarity with the second gated PET image). As described in connection with 910, the candidate CT images may be determined according to Equation (4). The motion vector field determination unit 520 may then determine the coefficient $\alpha$ and the motion vector field $\alpha T_{1\to 2}$ corresponding to the identified candidate CT image that has a highest similarity to the second gated PET image. The motion vector field $\alpha T_{1\to 2}$ may be designated as the PET-CT motion vector field between the second gated PET image and the CT image.

In some embodiments, the coefficient $\alpha$ that maximizes the similarity between the candidate CT image and the second gated PET image may be determined according to Equation (12) below:

$$\alpha = \underset{\alpha \in R}{\mathrm{argmax}}(D(P_2(x), C'(x))) = \underset{\alpha \in R}{\mathrm{argmax}}(D(P_2(x), C(x+\alpha T_{1\to 2}))) \qquad (12)$$

Examples

The following examples are provided for illustration purposed and not intended to limit the scope of the present disclosure.

Figure 10:
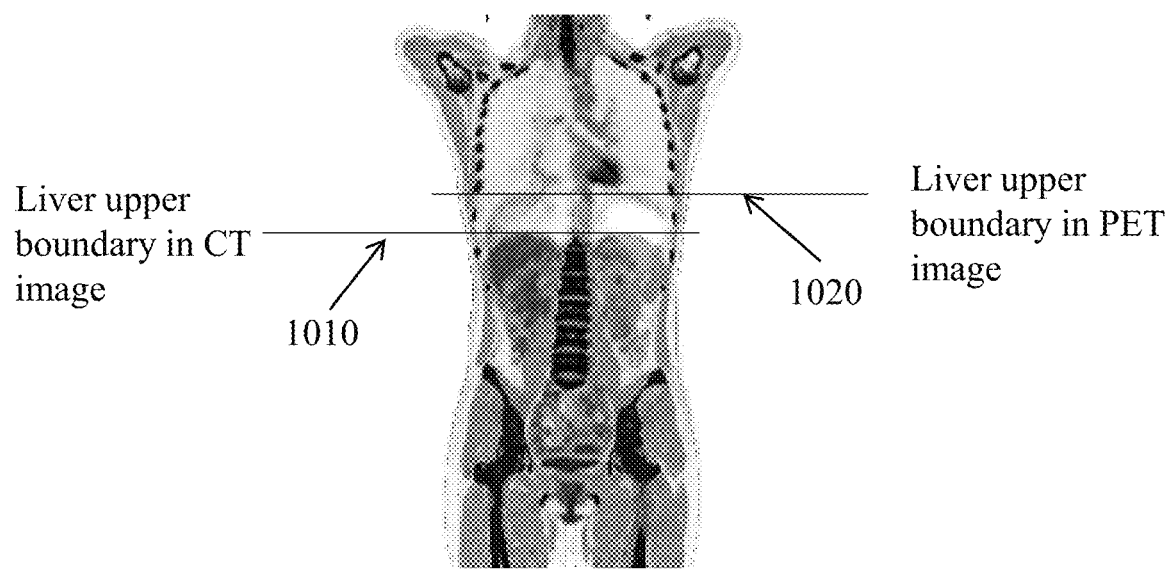
FIG. 10 illustrates an exemplary attenuation corrected PET image reconstructed based on PET data and a CT attenuation map without matching the PET data and the CT attenuation map according to some embodiments of the present disclosure.

FIG. 10 illustrates an exemplary attenuation corrected PET image reconstructed based on PET data and a CT attenuation map without matching the PET data and the CT attenuation map according to some embodiments of the present disclosure. The CT attenuation map was acquired when the patient remained in the deep inspiration breath-hold status. The PET data was acquired when the patient was in a breathing status. The PET data and the CT attenuation map were not matched before reconstruction with respect to motion phase. The image shows that the respiratory motion of the patient in the acquisition of the PET data leads to a mismatch of the PET image and the CT attenuation map. As shown in FIG. 10, the line 1010 indicates an upper boundary of the liver in the CT attenuation map and the line 1020 indicates an upper boundary of the liver in the PET image, which shows a mismatch between the PET image and the CT attenuation map with respect to the position of the liver.

Figure 11:
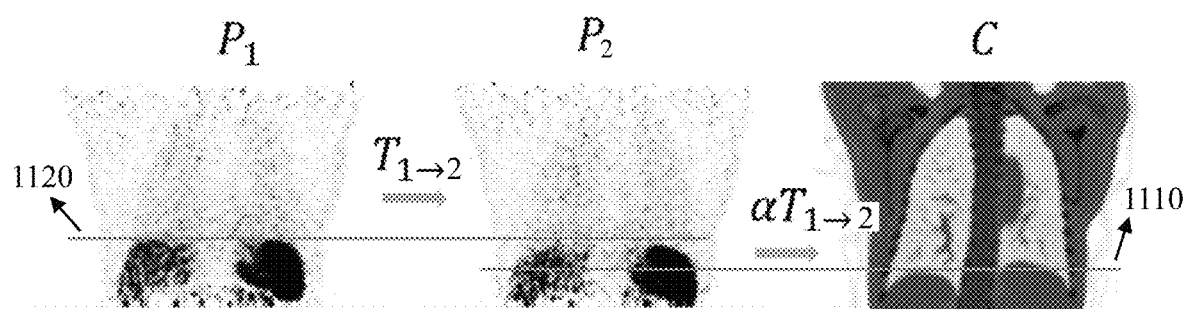
FIG. 11 illustrates exemplary gated PET images and a CT image according to some embodiments of the present disclosure.

FIG. 11 illustrates exemplary gated PET images and a CT image according to some embodiments of the present disclosure. $P_1$ is a first gated PET image corresponding to an end-expiratory phase, $P_2$ is a second gated PET image corresponding to an end-inspiratory phase, and C is a CT image corresponding to a deep inspiration breath-hold status. The same portion (e.g., an organ, a tissue, etc.) of the subject in the CT image corresponding to the deep inspiration breath-hold status may be different from that in the first and the second gated PET images. For example, position of the liver in the CT image (indicated by the line 1110) on a coronal plane was lower than that in the first gated PET image (indicated by the line 1120) and in the second gated PET image (not shown in FIG. 11).

$T_{1\rightarrow2}$ is a PET motion vector field between the first gated PET image corresponding to the end-expiratory phase and the second gated PET image corresponding to an end-inspiratory phase. The respiratory motion between the end-inspiratory phase and the deep inspiration breath-hold status was similar to that between the end-expiratory phase and the end-inspiratory phase. The motion vector field between the CT image and the second gated PET image may be $\alpha$ times of $T_{1\rightarrow2}$, where $\alpha$ was determined by performing process 900 as described in connection with FIG. 9.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "module," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the descriptions, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

We claim:

1. An imaging method implemented on at least one machine each of which has at least one processor and storage, the method comprising:
   obtaining an anatomical image of a scanning area of a subject acquired when the subject remains in a breath-hold status;
   obtaining positron emission tomography (PET) data of the scanning area of the subject, the PET data corresponding to a respiration signal with a plurality of respiratory phases of the subject, the respiratory phases including a first respiratory phase and a second respiratory phase;
   gating the PET data into a plurality of bins based on the plurality of respiratory phases of the respiration signal;
   reconstructing, based on the gated PET data, a plurality of gated PET images corresponding to the plurality of respiratory phases, the plurality of gated PET images including a first gated PET image corresponding to the first respiratory phase and a second gated PET image corresponding to the second respiratory phase;
   determining a first motion vector field between the first gated PET image and the second gated PET image;
   determining, based on the first motion vector field, a second motion vector field between the anatomical image and the second gated PET image; and
   reconstructing an attenuation corrected PET image based on the PET data, the second motion vector field, and the anatomical image, wherein the attenuation corrected PET image corresponds to a certain respiratory phase including a reference respiratory phase or an average of the plurality of respiratory phases.

2. The method of claim 1, wherein:
   the breath-hold status is a deep inspiration breath-hold status, the first respiratory phase is an end-expiratory phase, and the second respiratory phase is an end-inspiratory phase, or
   the breath-hold status is a deep expiration breath-hold status, the first respiratory phase is the end-inspiratory phase, and the second respiratory phase is the end-expiratory phase.

3. The method of claim 1, wherein the determining a first motion vector field between the first gated PET image and the second gated PET image further comprises:
   registering the first gated PET image with the second gated PET image; and
   determining, based on the registration between the first gated PET image and the second gated PET image, the first motion vector field.

4. The method of claim 1, wherein the attenuation corrected PET image corresponds to the reference respiratory phase, and the reconstructing the attenuation corrected PET image based on the PET data, the second motion vector field, and the anatomical image further comprises:
   determining the reference respiratory phase among the plurality of respiratory phases;
   obtaining, among the plurality of gated PET images, a reference gated PET image corresponding to the reference respiratory phase;
   determining, for each of the plurality of gated PET images, a third motion vector field between the gated PET image and the reference gated PET image;
   reconstructing, for each of the plurality of respiratory phases, a first PET image corresponding to the respiratory phase based on the second motion vector field;
   transforming, for each of the plurality of respiratory phases, the first PET image corresponding to the respiratory phase to a second PET image corresponding to the reference respiratory phase based on the corresponding third motion vector field; and
   generating the attenuation corrected PET image corresponding to the reference respiratory phase based on the plurality of second PET images.

5. The method of claim 4, further comprising:
   transforming the attenuation corrected PET image corresponding to the reference phase to an attenuation corrected PET image corresponding to one of the plurality of respiratory phases based on the corresponding third motion vector between the respiratory phase and the reference respiratory phase.

6. The method of claim 4, wherein the reconstructing a first PET image corresponding to each of the plurality of respiratory phases based on the second motion vector field further comprises:
   for each gated PET image corresponding to each of the plurality of respiratory phases, determining a fourth motion vector field between the gated PET image and the second gated PET image;

determining a fifth motion vector field between the gated PET image and the anatomical image based on the fourth motion vector field and the second motion vector field;

correcting the anatomical image based on the fifth motion vector field to obtain a corrected anatomical image corresponding to the respiratory phase; and reconstructing a first PET image corresponding to the respiratory phase based on the gated PET data and the corrected anatomical image.

7. The method of claim 1, wherein the attenuation corrected PET image corresponds to the average of the plurality of respiratory phases, and the reconstructing the attenuation corrected PET image based on the PET data, the second motion vector field, and the anatomical image further comprising:

reconstructing, for each respiratory phase, a first PET image corresponding to the respiratory phase; and obtaining the attenuation corrected PET image corresponding to the average of the plurality of respiratory phases by summing the first images corresponding to the plurality of respiratory phases.

8. The method of claim 1, wherein the attenuation corrected PET image corresponds to the average of the plurality of respiratory phases, and the reconstructing the attenuation corrected PET image based on the PET data, the second motion vector field, and the anatomical image further comprising:

generating, for each respiratory phase, a corrected anatomical image corresponding to the respiratory phase;

generating an average corrected anatomical image by summing the corrected anatomical images corresponding to the plurality of respiratory phases; and reconstructing, based on the PET data and the average corrected anatomical image, the attenuation corrected PET image corresponding to the average of the plurality of respiratory phases.

9. The method of claim 1, wherein the determining a second motion vector field between the second gated PET image and the anatomical image further comprises:

determining a plurality of candidate anatomical images based on the anatomical image and the first motion vector field;

determining, for each of the candidate anatomical images, a similarity between the second gated PET image and the candidate anatomical image;

identifying a highest similarity among the determined similarities; and determining, based on the identified highest similarity, the second motion vector field between the second gated PET image and the candidate anatomical image associated with the highest similarity.

10. The method of claim 1, wherein the anatomical image is at least one of a computed tomography (CT) image or a magnetic resonance (MR) image.

11. An imaging method implemented on at least one machine each of which has at least one processor and storage, the method comprising:

obtaining an anatomical image of a scanning area of a subject, the anatomical image being unaffected by respiratory motion;

obtaining positron emission tomography (PET) data of the scanning area of the subject, the PET data being affected by a respiratory motion of the subject;

binning the PET data into a plurality of respiratory phases of the respiratory motion of the subject, the plurality of respiratory phases including a first respiratory phase and a second respiratory phase;

reconstructing, based on the binned PET data, a plurality of gated PET images;

determining a target motion vector field between the anatomical image and a target gated PET image among the plurality of gated PET images, wherein the determining a target motion vector field between the anatomical image and a target gated PET image among the plurality of gated PET images comprises:

determining a first motion vector field between a first gated PET image corresponding to the first respiratory phase and a second gated PET image corresponding to the second respiratory phase;

determining a second motion vector field between the anatomical image and the second gated PET image based on the first motion vector field; and determining the target motion vector field between the anatomical image and the target gated PET image based on the first motion vector field and the second motion vector field; and generating, based on the anatomical image and the target motion vector field, an attenuation corrected target gated PET image by performing a phase-matched attenuation correction on the target gated PET data, wherein the attenuation corrected PET image corresponds to a certain respiratory phase including a reference respiratory phase or an average of the plurality of respiratory phases.

12. The method of claim 11, wherein:

the anatomical image is acquired when the subject remains in a deep inspiration breath-hold status, the first respiratory phase is an end-expiratory phase, and the second respiratory phase is an end-inspiratory phase, or the anatomical image is acquired when the subject remains in a deep expiration breath-hold status, the first respiratory phase is the end-inspiratory phase, and the second respiratory phase is the end-expiratory phase.

13. The method of claim 11, wherein the generating an attenuation corrected target gated PET image by performing a phase-matched attenuation correction on the target gated PET data further comprises:

determining a phase-matched anatomical image corresponding to the target gated PET image by applying the target motion vector field to the anatomical image; and performing the phase-matched attenuation correction on the target gated PET data based on the phase-matched anatomical image to generate the attenuation corrected target gated PET image.

14. The method of claim 13, wherein the phase-matched anatomical image and the target gated PET data corresponds to a same respiratory phase.

15. A system, comprising:

at least one non-transitory storage medium including a set of instructions for reconstructing a positron emission tomography (PET) image; and at least one processor configured to communicate with the at least one non-transitory storage medium, wherein when executing the set of instructions, the system is directed to:

obtain an anatomical image of a scanning area of a subject acquired when the subject remains in a breath-hold status;

obtain PET data of the scanning area of the subject, the PET data corresponding to a respiration signal with a plurality of respiratory phases of the subject, the respiratory phases including a first respiratory phase and a second respiratory phase;

gate the PET data into a plurality of bins based on the plurality of respiratory phases of the respiration signal;

reconstruct, based on the gated PET data, a plurality of gated PET images corresponding to the plurality of respiratory phases, the plurality of gated PET images including a first gated PET image corresponding to the first respiratory phase and a second gated PET image corresponding to the second respiratory phase;

determine a first motion vector field between the first gated PET image and the second gated PET image;

determine, based on the first motion vector field, a second motion vector field between the anatomical image and the second gated PET image; and reconstruct an attenuation corrected PET image based on the PET data, the second motion vector field, and the anatomical image, wherein the attenuation corrected PET image corresponds to a certain respiratory phase including a reference respiratory phase or an average of the plurality of respiratory phases.

16. The system of claim 15, wherein:

the breath-hold status is a deep inspiration breath-hold status, the first respiratory phase is an end-expiratory phase, and the second respiratory phase is an end-inspiratory phase, or the breath-hold status is a deep expiration breath-hold status, the first respiratory phase is the end-inspiratory phase, and the second respiratory phase is the end-expiratory phase.

17. The system of claim 15, wherein the attenuation corrected PET image corresponds to the reference respiratory phase, and the reconstructing the attenuation corrected PET image based on the PET data, the second motion vector field, and the anatomical image, the system is further directed to:

determine the reference respiratory phase among the plurality of respiratory phases;

obtain, among the plurality of gated PET images, a reference gated PET image corresponding to the reference respiratory phase;

determine, for each of the plurality of gated PET images, a third motion vector field between the gated PET image and the reference gated PET image;

reconstruct, for each of the plurality of respiratory phases, a first PET image corresponding to the respiratory phase based on the second motion vector field;

transform, for each of the plurality of respiratory phases, the first PET image corresponding to the respiratory phase to a second PET image corresponding to the reference respiratory phase based on the corresponding third motion vector field; and generate the attenuation corrected PET image corresponding to the reference respiratory phase based on the plurality of second PET images.

18. The system of claim 17, wherein to reconstruct a first PET image corresponding to each of the plurality of respiratory phases based on the second motion vector field, the system is further directed to:

for each gated PET image corresponding to each of the plurality of respiratory phases, determine a fourth motion vector field between the gated PET image and the second gated PET image;

determine a fifth motion vector field between the gated PET image and the anatomical image based on the fourth motion vector field and the second motion vector field;

correct the anatomical image based on the fifth motion vector field to obtain a corrected anatomical image corresponding to the respiratory phase; and reconstruct a first PET image corresponding to the respiratory phase based on the gated PET data and the corrected anatomical image.

19. The system of claim 17, wherein the system is further directed to:

transform the attenuation corrected PET image corresponding to the reference phase to an attenuation corrected PET image corresponding to one of the respiratory phases based on the corresponding third motion vector between the respiratory phase and the reference respiratory phase.

20. The system of claim 15, wherein to determine the second motion vector field between the second gated PET image and the anatomical image, the system is further directed to:

determine a plurality of candidate anatomical images based on the anatomical image and the first motion vector field;

determine, for each of the candidate anatomical images, a similarity between the second gated PET image and the candidate anatomical image;

identify a highest similarity among the determined similarities; and determine, based on the identified highest similarity, the second motion vector field between the second gated PET image and the candidate anatomical image associated with the highest similarity.

* * * * *